US008678589B2

(12) United States Patent
Sakata et al.

(10) Patent No.: US 8,678,589 B2
(45) Date of Patent: Mar. 25, 2014

(54) GAZE TARGET DETERMINATION DEVICE AND GAZE TARGET DETERMINATION METHOD

(75) Inventors: Kotaro Sakata, Hyogo (JP); Shigenori Maeda, Kyoto (JP); Ryo Yonetani, Kyoto (JP); Hiroaki Kawashima, Kyoto (JP); Takatsugu Hirayama, Kyoto (JP); Takashi Matsuyama, Kyoto (JP)

(73) Assignee: Panasonic Corporation, Osaka (JP)

( * ) Notice: Subject to any disclaimer, the term of this patent is extended or adjusted under 35 U.S.C. 154(b) by 371 days.

(21) Appl. No.: 13/057,857

(22) PCT Filed: Jun. 3, 2010

(86) PCT No.: PCT/JP2010/003700
§ 371 (c)(1),
(2), (4) Date: Feb. 7, 2011

(87) PCT Pub. No.: WO2010/143377
PCT Pub. Date: Dec. 16, 2010

(65) Prior Publication Data
US 2011/0141010 A1      Jun. 16, 2011

(30) Foreign Application Priority Data
Jun. 8, 2009   (JP) ................................ 2009-137647

(51) Int. Cl.
*A61B 3/14*  (2006.01)
(52) U.S. Cl.
USPC ............ 351/209; 351/211; 351/237; 351/246
(58) Field of Classification Search
USPC .......... 351/209–212, 200, 204, 205, 237, 246
See application file for complete search history.

(56) References Cited

U.S. PATENT DOCUMENTS

| 4,239,351 A * | 12/1980 | Williams et al. ............. 351/243 |
| 2006/0132319 A1 | 6/2006 | Isaji et al. |

(Continued)

FOREIGN PATENT DOCUMENTS

| JP | 2002-183212 | 6/2002 |
| JP | 2004-62393 | 2/2004 |

(Continued)

OTHER PUBLICATIONS

International Search Report issued Jun. 29, 2010 in International (PCT) Application No. PCT/JP2010/003700.

(Continued)

*Primary Examiner* — Darryl J Collins
*Assistant Examiner* — Gary O'Neill
(74) *Attorney, Agent, or Firm* — Wenderoth, Lind & Ponack, L.L.P.

(57) ABSTRACT

A gaze target determination device includes an event setting unit that generates, for each object at different times, a display event which triggers a movement of the gaze direction of the user who is gazing at the object and which indicates a movement or a change of the object; and a gaze trajectory calculation unit that calculates a gaze trajectory based on the detected user's gaze direction. An eye movement event detection unit detects an event detection time which is a time at which the gaze direction moves according to the display event, based on the calculated gaze trajectory. A synchronization structure analysis unit calculates, for each object, time difference between the event detection time and event occurrence time; and a gaze target determination unit determines the object at which the user is gazing from among the objects, based on the calculated time difference.

12 Claims, 18 Drawing Sheets

(56) References Cited

U.S. PATENT DOCUMENTS

| | | | |
|---|---|---|---|
| 2009/0086165 A1* | 4/2009 | Beymer | 351/210 |
| 2009/0128311 A1 | 5/2009 | Nishimura et al. | |
| 2010/0220897 A1* | 9/2010 | Ueno et al. | 382/115 |

FOREIGN PATENT DOCUMENTS

| | | |
|---|---|---|
| JP | 2005-143599 | 6/2005 |
| JP | 2005-245598 | 9/2005 |
| JP | 2006-158740 | 6/2006 |
| JP | 2008-288707 | 11/2008 |
| JP | 4203279 | 12/2008 |
| WO | 2007/069489 | 6/2007 |
| WO | 2007/148465 | 12/2007 |

OTHER PUBLICATIONS

Hirotake Yamazoe et al., "*Remote and Head-Motion-Free Gaze Tracking with Automated Head-Eye Model Calibrations*", Meeting on Image Recognition & Understanding (MIRU2008), pp. 1650-1655, Jul. 2008 with partial English Translation (p. 1651, right column, lines 36 to 44).

The Vision Society of Japan: "*Handbook of Visual Information Processing*", Asakura Publishing Company Ltd., p. 392, Sep. 2000 with partial English translation (p. 392, the first item of Table 9.2).

Ryo Yonetani et al., "*Gazed Object Estimation Using the Timing Structure between Displayed Events and Eye Movements*", Information Processing Society of Japan, pp. 1-8, Jun. 2009 with partial English translation (abstract).

Ryo Yonetani et al., "*Gaze Probing: Event-Based Estimation of Gazed Object*", Meeting on Image Recognition & Understanding (MIRU2009), Jul. 2009 with partial English translation (abstract).

Takamasa Okamoto et al., "*Gazed Object Estimation Based on Relation Between the Movements of Gaze Direction and Object*", Meeting on Image Recognition & Understanding (MIRU2006), pp. 31 to pp. 36, Jul. 2006 with partial English translation (abstract).

\* cited by examiner

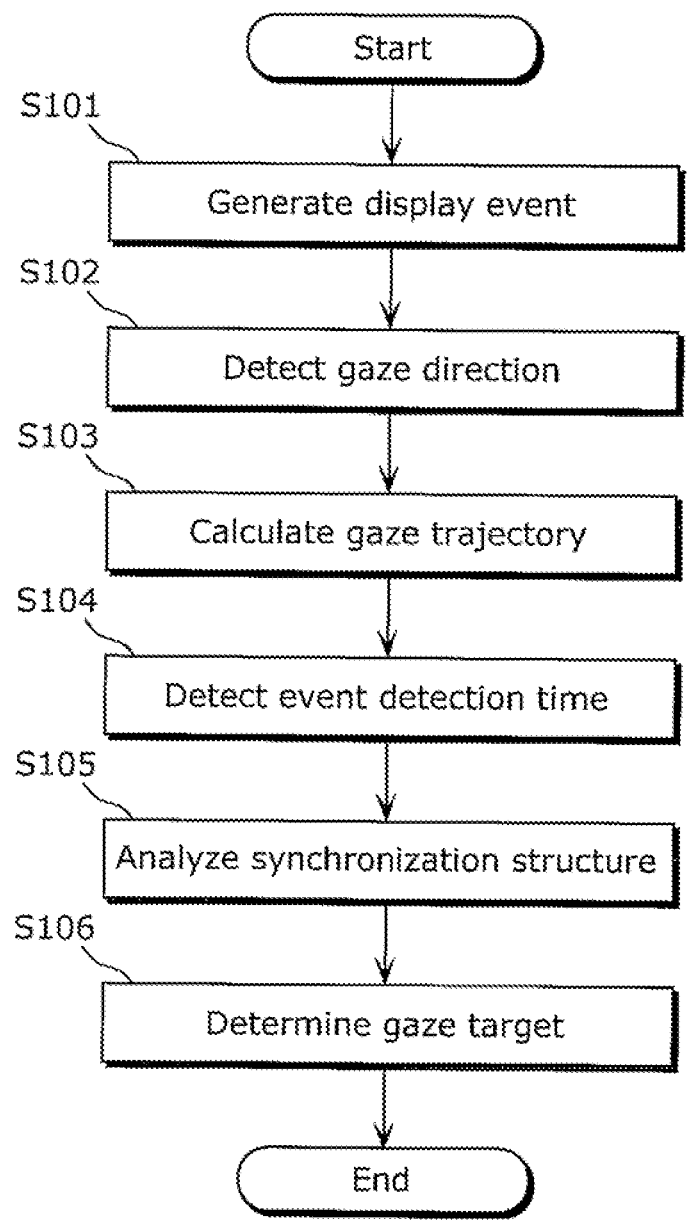

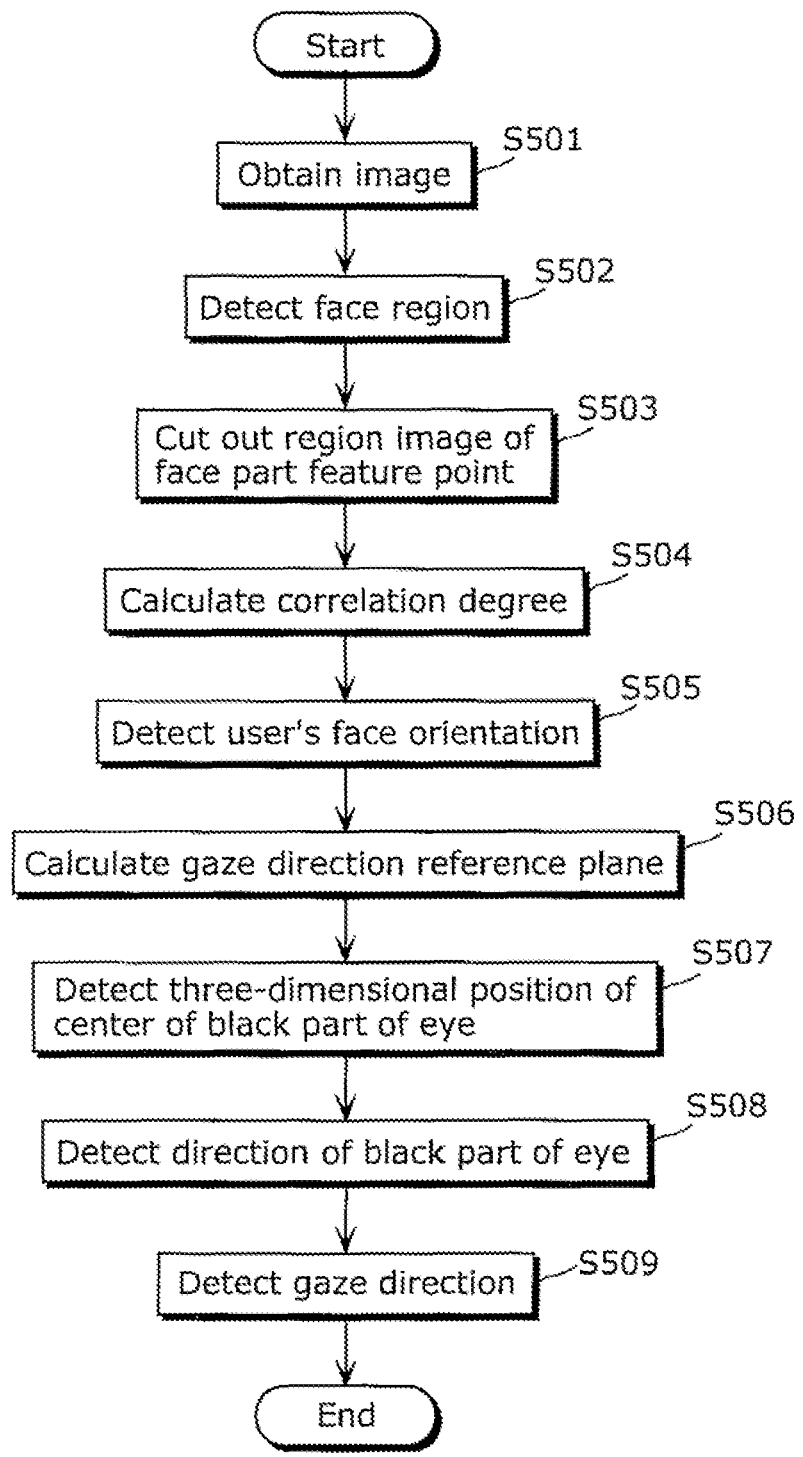

FIG. 10
(a) Definition of display event
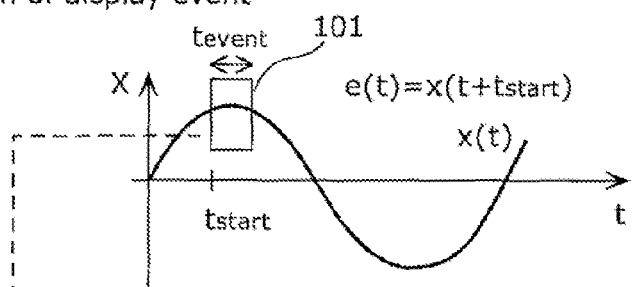
(b) Movement trajectory of object
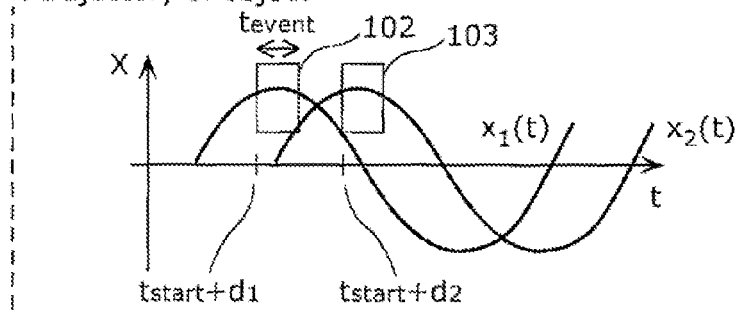
(c) Gaze trajectory
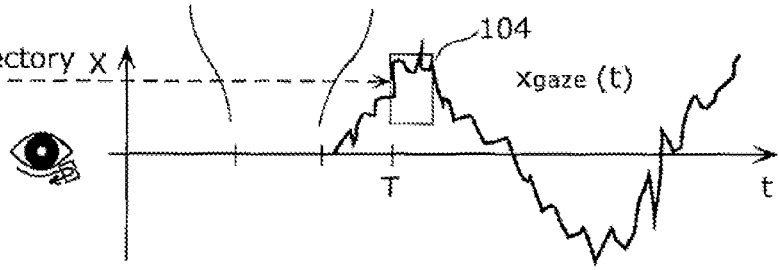

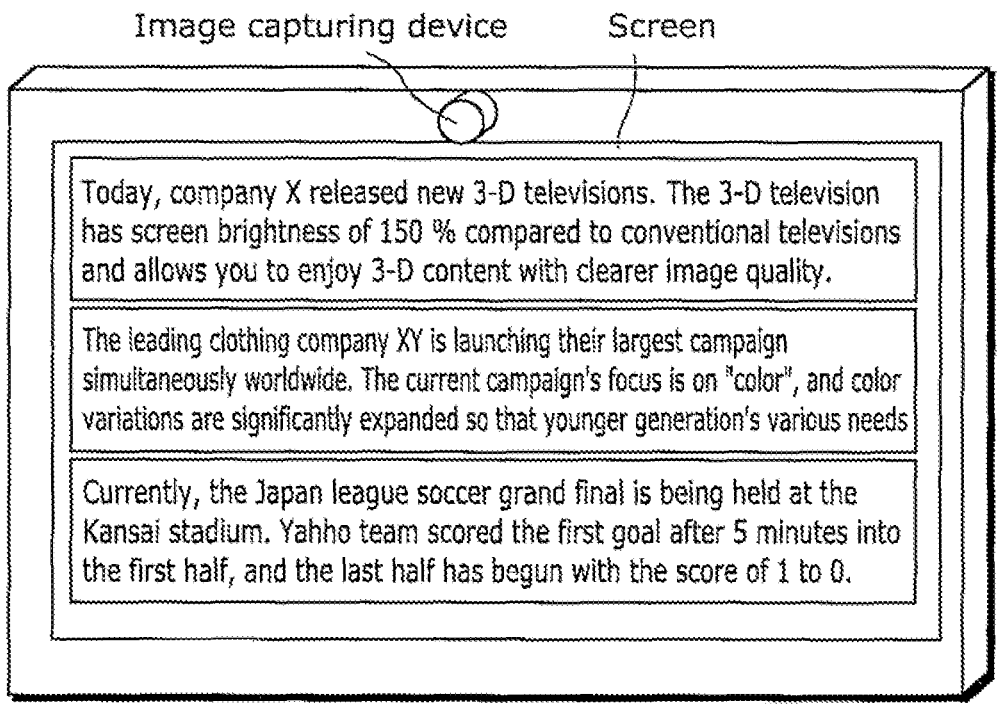

GAZE TARGET DETERMINATION DEVICE AND GAZE TARGET DETERMINATION METHOD

BACKGROUND OF INVENTION

1. Technical Field

The present invention relates to a gaze target determination device which determines the object at which a user is gazing from among a plurality of objects displayed on a screen.

2. Background Art

Generally, the position of gaze on a screen obtained from eye gaze direction of a user is compared with a position of an object displayed on the screen to determine the object at which the user is gazing (hereinafter, may be simply referred to as a "gaze target"). Examples of a method for detecting an eye gaze direction include a corneal reflex method that estimates the gaze direction utilizing the positions of a pupil and a light source image (Purkinje image) that is a reflection, on a cornea, of near-infrared light irradiated on an eye by a light emitting diode (LED). Another example of a method for detecting an eye gaze is a method that detects the gaze direction utilizing a three-dimensional eye model or the like based on a user image captured by a video camera, assuming that a three-dimensional vector connecting the center of an eyeball and the center of an iris is the gaze direction (see for example, Non Patent Literature 1).

However, in the corneal reflex method, infrared light needs to be irradiated on the eye area; and thus, the detection range of the eye gaze is limited to the range where the infrared light can be irradiated. Thus, the corneal reflex method has a limitation in the user's posture or standing position where the eye gaze direction can be detected.

In the method disclosed in Non Patent Literature 1, it is not possible to directly measure the center position of an eyeball, the radius of the eyeball, or the like; and thus, parameters such as the eye center position or the radius of the eye are modeled using facial features. The estimation of the gaze direction with use of the three-dimensional eye model has an advantage that the user can take any postures or standing positions freely. On the other hand, a disadvantage also exists where a relatively large error may occur between the line connecting the eyeball center and the iris center and the actual eye gaze due to an error in calibration for the user or an error in the facial feature detection. In order to reduce such errors, there are proposed methods that aim to improve the accuracy of the gaze detection using multiple cameras having different viewpoints. However, in this type of method, the estimation accuracy of the gaze direction is still not significantly improved.

As described, in the case where the user takes various postures freely to some extent, the estimated gaze direction includes a relatively large error. Thus, in order to accurately determine the gaze target, there are possible approaches which focus on the tracking capability of the eye gaze relative to a change in an object on a screen, instead of directly comparing the gaze position obtained from the gaze direction with the display position of an object (see Patent Literature 1 and Patent Literature 2).

The attention determination device disclosed in Patent Literature 1 moves display information Q displayed on a screen, when the gaze is directed on the screen. When the detected gaze movement direction corresponds with the movement of the display information Q, the attention determination device determines that the gaze tracked the movement of the display information Q.

The driver's condition determining device disclosed in Patent Literature 2 gives a driver a visual stimulus. The driver's condition determining device also determines whether or not the driver is in the conditions suited for driving, based on detection results of the driver's gaze direction, gaze duration time, and a gaze trajectory when the position to which the stimulus is given is moved.

CITATION LIST

Patent Literature

[PTL 1]
Patent Literature 1 Japanese Patent No. 4203279
[PTL 2]
Patent Literature 2 Japanese Unexamined Patent Application Publication No. 2006-158740

[Non Patent Literature]

[NPL 1]
Non-Patent Literature 1 Hirotake YAMAZOE, Akira UTSUMI, Takako YONEZAWA, Shinji ABE, "Remote Gaze Estimation by a Single Camera using 3D Eye Model", Meeting on Image Recognition & Understanding (MIRU2008), pp. 1650 to 1655, 2008.

SUMMARY OF INVENTION

However, the conventional techniques merely determine the gaze tracking the movement of one object. Thus, a problem exists where in the case where multiple objects made changes such as movement, it is not possible to find out to which object's change the reaction of the gaze of the user was made.

The present invention has been conceived to solve the conventional problem and has an object to provide a gaze target determination device which can accurately determine the object at which the user is gazing, from among a plurality of objects displayed on the screen.

In order to achieve the object, a gaze target determination device according to an aspect of the present invention is a gaze target determination device which determines an object at which a user is gazing from among a plurality of objects displayed on a screen. The gaze target determination device includes: an event setting unit which generates a display event for each of the objects at different times, the display event triggering a movement of a gaze direction of the user who is gazing at the object, the display event indicating at least one of a movement and a change of at least part of the object; a gaze direction detection unit which detects the gaze direction of the user; a gaze trajectory calculation unit which calculates a gaze trajectory that is time series data of the gaze direction, based on the gaze direction detected by the gaze direction detection unit; an eye movement event detection unit which detects an event detection time which is a time at which the gaze direction moves according to the display event, based on the gaze trajectory calculated by the gaze trajectory calculation unit; a synchronization structure analysis unit which calculates, for each of the objects, a time difference between the event detection time detected by the eye movement event detection unit and an event occurrence time that is a time at which the display event is generated by the event setting unit; and a gaze target determination unit which determines the object at which the user is gazing from among the objects, based on the time difference calculated by the synchronization structure analysis unit.

With such a structure, it is possible to determine the gaze target of the user based on the time difference between the event detection time and the event occurrence time. This allows accurate determination of the object at which the user is gazing from among a plurality of objects displayed on a screen. Furthermore, the gaze target is determined based on, not the gaze position, but the movement of the gaze direction; and thus, it is possible to accurately determine the gaze target even when the detection accuracy of the gaze direction is low.

Further, it is preferable that the gaze target determination unit determines, as the object at which the user is gazing, an object for which the time difference that is equal to or greater than a reference time difference and that is closest to the reference time difference is calculated.

With such a structure, it is possible to exclude determination of, as the gaze target, the object for which the time difference less than latent time is detected. The latent time here is time period required before the eye starts tracking the movement of the object in a smooth eye movement. This allows determination of the gaze target with higher accuracy.

Further, it is preferable that the display event triggers a movement of the gaze direction greater than an error in the gaze direction detection performed by the gaze direction detection unit.

With such a structure, it is possible to reduce false determination of the gaze target due to an error in the eye gaze detection, allowing determination of the gaze target with higher accuracy.

It is preferable that the display event indicates a movement of at least part of the object, and the eye movement event detection unit detects the event detection time, based on a similarity between a trajectory of the movement indicated by the display event and the gaze trajectory.

With such a structure, it is possible to determine the gaze target based on the movement trajectory of an object and the movement of the gaze direction; and thus, it is possible to accurately determine the gaze target even when the detection accuracy of the gaze direction is low.

It is preferable that the display event indicates a movement including a change of a moving direction, and the event setting unit generates the display event by reciprocating at least part of each of the objects.

With such a structure, it is possible to detect the event detection time from the gaze trajectory using characteristic movement trajectories, which allows improvement in the detection accuracy of the event detection time. As a result, it is possible to accurately determine the gaze target.

Further, it is preferable that the display event indicates a movement of at least part of the object in a horizontal direction.

With such a structure, it is possible to determine the gaze target with higher accuracy using characteristics of human eyes where the gaze movement in the horizontal direction is more easily detected than in the vertical direction.

Further, it is preferable that the display event triggers the movement, at a speed equal to or higher than a predetermined speed, of the gaze direction of the user who is gazing at the object, and the eye movement event detection unit detects the event detection time which is a time at which the gaze direction moves at a speed equal to or higher than the predetermined speed, based on the gaze trajectory calculated by the gaze trajectory calculation unit.

With such a structure, it is possible to determine the gaze target based on the moving speed of the gaze direction; and thus, it is possible to accurately determine the gaze target even when the detection accuracy of the gaze direction is low.

Further, it is preferable that each of the objects includes a character string, the display event triggers the movement, at a speed equal to or higher than the predetermined speed, of the gaze direction of the user who is gazing at the object to read the character string, and the event setting unit generates the display event by changing a character included in the character string from an unreadable state where the user cannot read the character to a readable state where the user can read the character.

With such a structure, it is possible to accurately determine the gaze target of the user who is gazing at the object to read a character string.

Further, it is preferable that the display event indicates a change of an initial character included in the character string, from the unreadable state to the readable state, and the event setting unit generates the display event by changing the character included in the character string from the readable state to the unreadable state, and changing the initial character included in the character string from the unreadable state to the readable state.

With such a structure, it is possible to generate a display event while reducing the feeling of strangeness experienced by the user who is gazing at an object to read a character string.

Further, it is preferable that the display event indicates a change of an initial character included in the character string from the unreadable state to the readable state, and the event setting unit generates the display event by (i) changing, in reading order, the character included in the character string from the unreadable state to the readable state and further changing, in the reading order, the character that is in the readable state to be in the unreadable state, and (ii) changing the initial character included in the character string from the unreadable state to the readable state.

With such a structure, it is possible to generate a display event while reducing the feeling of strangeness experienced by the user who is gazing at an object to read a character string.

Further, it is preferable that the display event indicates a change in which a character-spacing increases in the character string, and the event setting unit generates the display event by moving the character string in one direction so that the character string passes through the object, and changing, in the character string, a character-spacing so that the character-spacing is larger than an immediately preceding character-spacing.

With such a structure, it is possible to generate a display event while reducing the feeling of strangeness experienced by the user who is gazing at an object to read a character string.

Further, it is preferable that the display event indicates a change of an initial character of a line included in the character string from the unreadable state to the readable state, and the event setting unit generates the display event by changing, in reading order, the character included in the character string from the unreadable state to the readable state, the character string including a plurality of line.

With such a structure, it is possible to generate a display event while reducing the feeling of strangeness experienced by the user who is gazing at an object to read a character string.

Further, it is preferable that the event setting unit generates the display event by moving the object at a speed equal to or higher than the predetermined speed.

With such a structure, it is possible to accurately determine the gaze target of the user, using that the gaze direction synchronizes with the movement of an object.

Further, an integrated circuit according to an aspect of the present invention is an integrated circuit which determines an object at which a user is gazing from among a plurality of objects displayed on a screen. The integrated circuit includes: an event setting unit configured to generate a display event for each of the objects at different times, the display event triggering a movement of a gaze direction of the user who is gazing at the object, the display event indicating at least one of a movement and a change of at least part of the object; a gaze direction detection unit configured to detect the gaze direction of the user; a gaze trajectory calculation unit configured to calculate a gaze trajectory that is time series data of the gaze direction, based on the gaze direction detected by the gaze direction detection unit; an eye movement event detection unit configured to detect an event detection time which is a time at which the gaze direction moves according to the display event, based on the gaze trajectory calculated by the gaze trajectory calculation unit; a synchronization structure analysis unit configured to calculate, for each of the objects, a time difference between the event detection time detected by the eye movement event detection unit and an event occurrence time that is a time at which the display event is generated by the event setting unit; and a gaze target determination unit configured to determine the object at which the user is gazing from is among the objects, based on the time difference calculated by the synchronization structure analysis unit.

With such a structure, it is possible to obtain the same advantageous effects as those of the gaze target determination device.

Further, a method for determining a gaze target according to an aspect of the present invention is a method for determining an object at which a user is gazing from among a plurality of objects displayed on a screen. The method includes: generating a display event for each of the objects at different times, the display event triggering a movement of a gaze direction of the user who is gazing at the object, the display event indicating at least one of a movement and a change of at least part of the object; detecting the gaze direction of the user; calculating a gaze trajectory that is time series data of the gaze direction, based on the gaze direction detected in the detecting of the gaze direction of the user; detecting an event detection time which is a time at which the gaze direction moves according to the display event, based on the gaze trajectory calculated in the calculating of a gaze trajectory; calculating, for each of the objects, a time difference between the event detection time detected in the detecting of an event detection time and an event occurrence time that is a time at which the display event is generated in the generating; and determining the object at which the user is gazing from among the objects, based on the time difference calculated in the calculating of a time difference.

With such a structure, it is possible to obtain the same advantageous effects as those of the gaze target determination device.

Note that the present invention can also be implemented as a program causing a computer to execute the respective steps included in the gaze target determination method. Such a program may be distributed, of course, via recording medium such as a CD-ROM (Compact Disc Read Only Memory) and communication medium such as the Internet.

With a gaze target determination device according to an aspect of the present invention, it is possible to determine the gaze target of the user based on time difference between event detection time and event occurrence time. This allows accurate determination of the object at which the user is gazing from among a plurality of objects displayed on a screen.

BRIEF DESCRIPTION OF DRAWINGS

FIG. 2 is a flowchart of processing of gaze target determination according to the embodiment of the present invention.

FIG. 4 is a flowchart of the processing of the gaze direction detection according to the embodiment of the present invention.

FIG. 10 is a diagram showing processing of event detection time detection according to the embodiment of the present invention.

FIG. 20 is a diagram showing an arrangement example of objects displayed on a screen according to Variation 5 of the embodiment of the present invention.

FIG. 21 is a diagram showing an example of a display event according to the Variation 5 of the embodiment of the present invention.

DETAILED DESCRIPTION OF INVENTION

Hereinafter, an embodiment of the present invention is described with reference to the drawings.

Generally, eye movement of a user tracks the movement of the object at which the user is gazing. Thus, there is a temporal synchronization structure between the movement of the object at which the user is gazing and the eye movement of the user. It is possible to determine the object at which the user is gazing by analyzing the synchronization structure. For the analysis of the synchronization structure, it is necessary to move or change an object so as to cause eye movement that can be easily detected even when an error in the detection of the gaze direction is large.

In the following description, a display event (event) refers to at least one of the characteristic movement and change of at least part of an object, which causes eye movement that can be easily detected even when an error in the detection of the gaze direction is large. Note that change of at least part of an object includes change of the shape, size, brightness, color or the like of at least part of an object, and also includes that at least part of an object appears or disappears.

Figure 1:
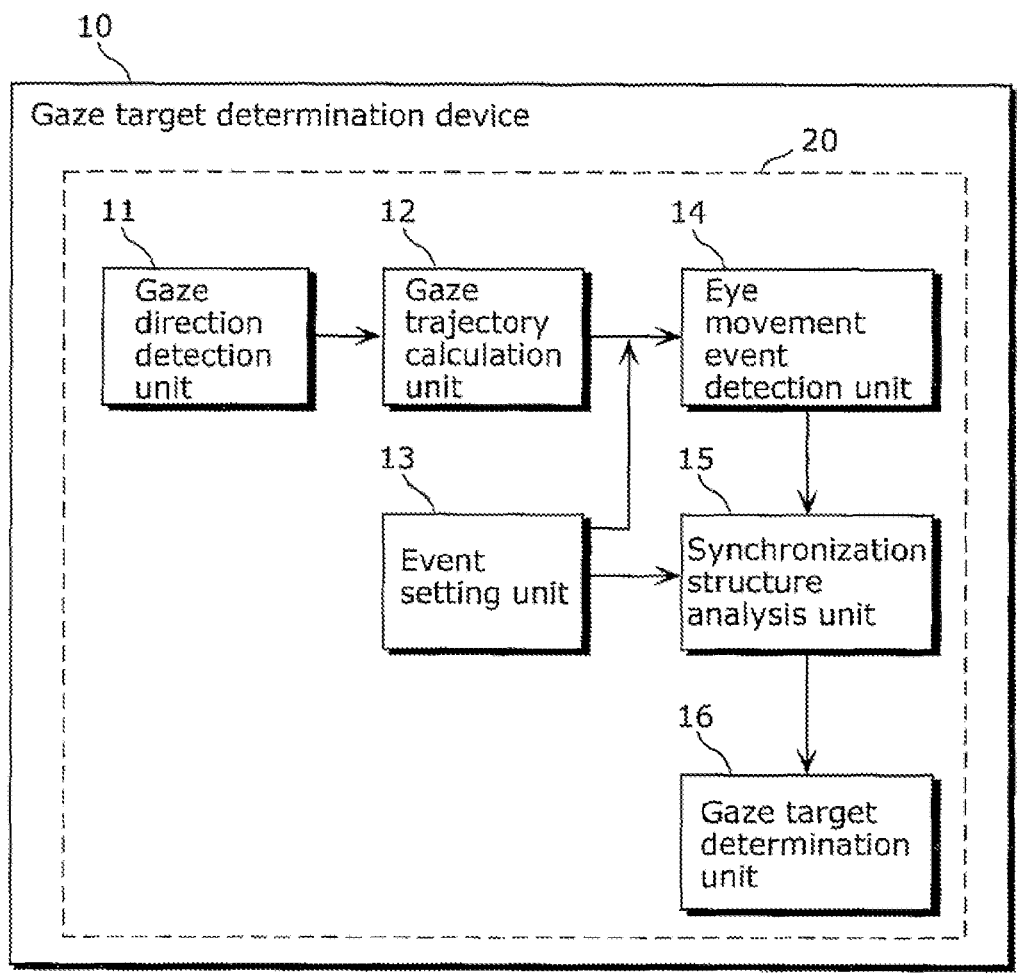
FIG. 1 is a block diagram showing functional structures of a gaze target determination device according to an embodiment of the present invention.

FIG. 1 is a block diagram showing functional structures of a gaze target determination device according to the embodiment of the present invention.

A gaze target determination device 10 determines the object at which a user is gazing from among a plurality of objects displayed on a screen. Here, an object refers to a display element or a collection of display elements displayed on a screen.

As shown in FIG. 1, the gaze target determination device 10 includes a gaze direction detection unit 11, a gaze trajectory calculation unit 12, an event setting unit 13, an eye movement event detection unit 14, a synchronization structure analysis unit 15, and a gaze target determination unit 16.

The gaze direction detection unit 11 detects the eye gaze direction of the user. In other words, the gaze direction detection unit 11 detects the direction at which the user is looking.

The gaze trajectory calculation unit 12 calculates the gaze trajectory that is time series data of the gaze direction, based on the gaze direction detected by the gaze direction detection unit 11. In other words, the gaze trajectory calculation unit 12 calculates the gaze trajectory indicating the movement of the gaze direction, based on the gaze direction detected by the gaze direction detection unit 11.

More particularly, the gaze trajectory calculation unit 12 calculates, for example, the movement trajectory of the gaze position of the user on a screen, as a gaze trajectory. In this case, the gaze trajectory calculation unit 12 calculates, as the gaze position, point at the intersection of the screen and the straight line extending from the user to the gaze direction, using the gaze direction and the position of the user. The gaze trajectory calculation unit 12 then calculates the movement trajectory of the gaze position thus calculated as the gaze trajectory. It is sufficient that the position of the user is detected using, for example, a parallax of a user image in a stereo image captured by a stereo camera or the like. Furthermore, for example, the position of the user may be detected using the pressure detected by a pressure sensor provided on the floor in front of the screen.

The event setting unit 13 sets, for each of the objects on the screen, a display event which starts at different times. In other words, the event setting unit 13 generates a display event for each of the objects displayed on the screen at different times.

Here, as described earlier, the display event refers to at least one of the movement and change of at least part of the object. In addition, the display event triggers the movement of the gaze direction of the user who is gazing at an object. In other words, the display event triggers eye movement of the user who is gazing at an object. More particularly, the display event triggers the movement of the gaze position of the user who is gazing at an object.

The eye movement event detection unit 14 extracts, from the gaze trajectory calculated by the gaze trajectory calculation unit 12, an interval which is highly correlated with a gaze trajectory template which is associated with a display event in advance. The gaze trajectory template is a gaze trajectory which is highly likely to occur when the user gazes at a display event.

In other words, the eye movement event detection unit 14 detects, as event detection time, time at which the gaze direction moves according to the display event, based on the gaze trajectory calculated by the gaze trajectory calculation unit 12. More particularly, the eye movement event detection unit 14 detects, as the event detection time, the start time of the time interval indicating the movement trajectory of the gaze position.

More particularly, the eye movement event detection unit 14 detects the event detection time based on a similarity between the movement trajectory indicated by the display event and the gaze trajectory. More specifically, the eye movement event detection unit 14 detects the event detection time by detecting, based on the gaze trajectory calculated by the gaze trajectory calculation unit 12, the time interval (event detection interval) indicating the movement trajectory of the gaze position similar to the movement trajectory of the object indicated by the display event.

The synchronization structure analysis unit 15 determines the time difference between the start time of the display event of each object and the start time of the interval detected by the eye movement event detection unit 14, as the synchronization degree of the gaze to the display event of each object.

In other words, the synchronization structure analysis unit 15 calculates, for each object, the time difference between the event detection time and the event occurrence time. Here, the event occurrence time refers to the time at which a display event is generated by the event setting unit 13. In other words, the event occurrence time is the time at which at least part of an object moves or changes as indicated by the display event. In the present embodiment, the start time of the event occurrence interval that is the time interval during which the display event is occurring corresponds to the event occurrence time.

The gaze target determination unit 16 determines the object having a high synchronization degree as the gaze target of the user. In other words, the gaze target determination unit 16 determines the object at which the user is gazing from among a plurality of objects, based on the time difference calculated by the synchronization structure analysis unit 15.

Next, reference is made to respective operations performed in the gaze target determination device 10.

FIG. 2 is a flowchart of the processing of the gaze target determination according to the embodiment of the present invention.

First, the event setting unit 13 generates a display event to each object at different times (S101)

At this time, the gaze direction detection unit 11 detects the gaze direction of the user (S102). Then, the gaze trajectory calculation unit 12 calculates the gaze trajectory based on the detected gaze direction (S103).

The processing of Step S101 and the processing of Steps S102 and S103 may be performed in parallel.

The eye movement event detection unit 14 detects the event detection time from the calculated gaze trajectory (S104). Subsequently, the synchronization structure analysis unit 15 calculates the time difference between the event detection time and the event occurrence time (S105).

Lastly, the gaze target determination unit 16 determine, based on the calculated time difference, the object at which the user is gazing from among a plurality of objects (S106).

In such a manner, the gaze target determination device 10 determines the object at which the user is gazing from among a plurality of objects.

Hereinafter, each processing included in the gaze target determination processing is described more in detail with reference to the drawings.

First, reference is made to the details of the gaze direction detection processing (S102) which detects the gaze direction.

In the present embodiment, the gaze direction is calculated based on the combination of the orientation of the user's face (hereinafter, referred to as face orientation) and the direction of the black part of the eye relative to the face orientation of the user (hereinafter, referred to as black-part-of-the eye direction). Thus, the gaze direction detection unit 11 first estimates the three-dimensional face orientation of a person. Next, the gaze direction detection unit 11 estimates the black-part-of-the-eye direction. Lastly, the gaze direction detection unit 11 calculates the gaze direction by using the face orientation and the black-part-of-the-eye direction.

The gaze direction detection unit 11 does not necessarily calculate the gaze direction based on the combination of the face orientation and the black-part-of-the-eye direction. For example, the gaze direction detection unit 11 may calculate the gaze direction based on the center of the eyeball and the center of the iris (black part of the eye). In other words, the gaze direction detection unit 11 may calculate, as the gaze direction, a three-dimensional vector connecting the three-dimensional position of the center of the eyeball and the three-dimensional position of the center of the iris (black part of the eye).

Figure 3A:
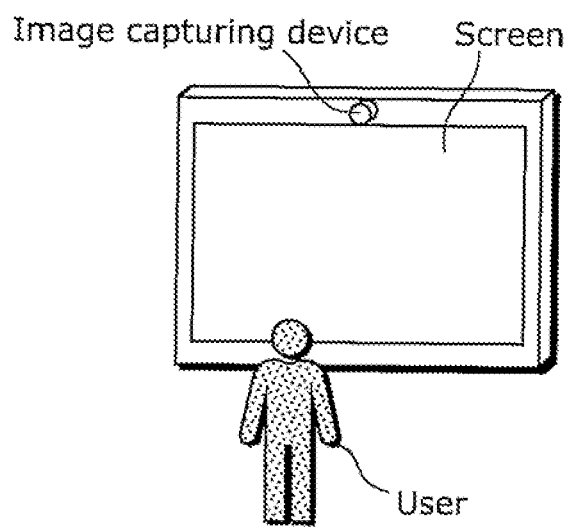
FIG. 3A is a diagram showing an image capturing device which captures an image obtained in gaze direction detection processing according to the embodiment of the present invention.
Figure 3B:
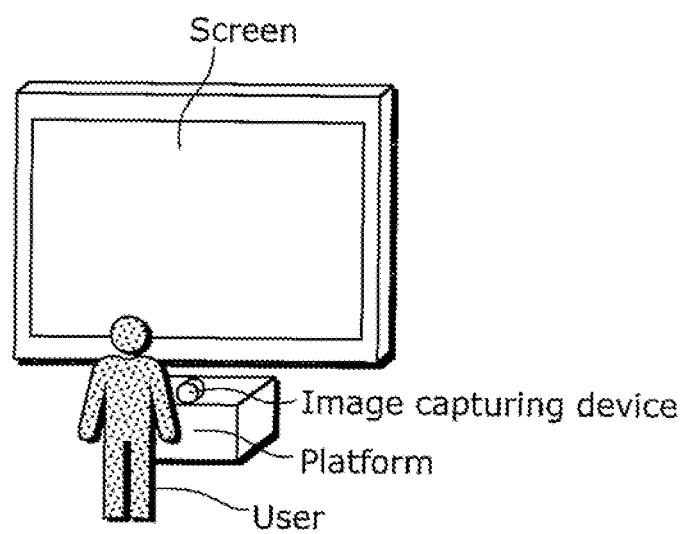
FIG. 3B is a diagram showing another image capturing device which captures an image obtained in the gaze direction detection processing according to the embodiment of the present invention.

FIGS. 3A and 3B are diagrams each showing an image capturing device which captures an image obtained in the gaze direction detection processing according to the embodiment of the present invention. As shown in FIG. 3A or FIG. 3B, the image capturing device is provided near the screen so that an image of the user in front of the screen can be captured.

FIG. 4 is a flowchart of the processing of the gaze direction detection according to the embodiment of the present invention.

First, the gaze direction detection unit 11 obtains an image, captured by the image capturing device, of the user who is in front of the screen (S501). The gaze direction detection unit 11 then detects a face region out of the obtained image (S502). Next, the gaze direction detection unit 11 applies, to the detected face region, regions each having a face part feature point, and cuts out a region image of each face part feature points (S503). Here, the face part feature point is associated with each reference face orientation.

The gaze direction detection unit 11 then calculates the correlation degrees between the cut out region image and pre-stored template images (S504). The gaze direction detection unit 11 calculates a sum of angles weighted based on the ratio of the calculated correlation degrees as the respective reference face orientations. Finally, the gaze direction detection unit 11 detects the weighted sum as the user's face orientation corresponding to the detected face region (S505).

Figure 5:
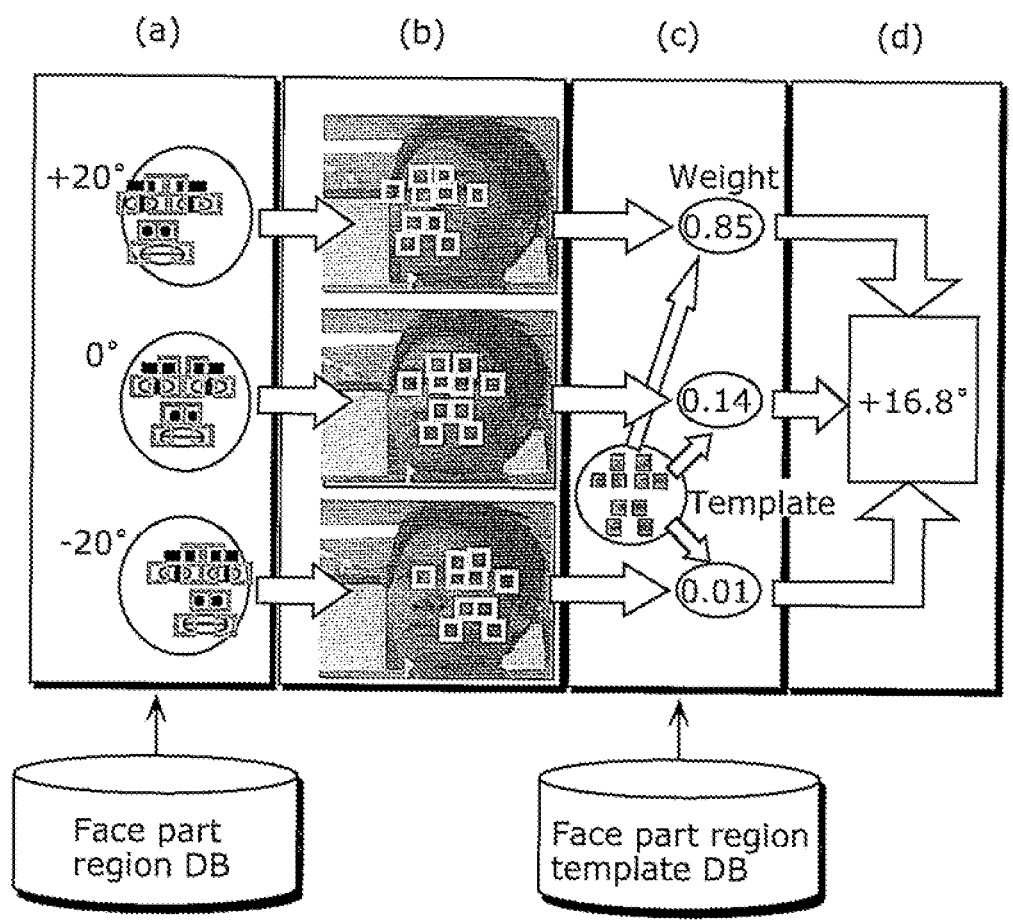
FIG. 5 is a diagram showing processing of face orientation detection in the gaze direction detection processing according to the embodiment of the present invention.

FIG. 5 is a diagram showing processing of face orientation detection in the gaze direction detection processing according to embodiment of the present invention.

As shown in (a) in FIG. 5, the gaze direction detection unit 11 reads out regions each having a face part feature point from a face part region database (DB) storing regions of face part feature points corresponding to each reference face orientation. As shown in (b) in FIG. 5, the gaze direction detection unit 11 then (i) applies the regions of the face part feature points to a face region of a captured image for each reference face orientation, and (ii) cuts out region images of the face part feature points for each reference face orientation.

As shown in (c) in FIG. 5, the gaze direction detection unit 11 then calculates, for each reference face orientation, the correlation degrees between the cut out region image and template images stored in the face part region template DB. The gaze direction detection unit 11 also calculates a weight for each reference face orientation according to the magnitude of the calculated correlation degree. For example, the gaze direction detection unit 11 calculates, as weight, the ratio of the correlation degree for each reference face orientation to the total sum of the degrees of correlation of the reference face orientations.

After that, as shown In (d) in FIG. 5, the gaze direction detection unit 11 calculates the total sum of the values each of which is obtained by multiplying the angle of the reference face orientation by the calculated weight, to detect the calculation result as the face orientation of the user.

In the example of (d) of FIG. 5, weighting and detection of the face orientation are as follows: an angle of a reference face orientation plus 20 degrees is weighted "0.85"; an angle of facing front is weighted "0.14"; and an angle of a reference face orientation minus 20 degrees is weighted "0.01". Thus, the gaze direction detection unit 11 detects the face orientation as 16.8 degrees (=20×0.85+0×0.14+(−20)×0.01).

In FIG. 5, the gaze direction detection unit 11 employs a region image having a face part feature point to calculate a correlation degree; however, the embodiment of the present invention is not limited to this. For example, the gaze direction detection unit 11 may calculate a correlation degree employing an image having the entire face region.

Other examples of the method for detecting a face orientation include a method which detects face part feature points, such as an eye, a nose, or a mouth, from a face image, and calculates the face orientation based on the positional relation of the face part feature points.

Examples of the method for calculating a face orientation based on the positional relation of the face part feature points includes a method which: (i) rotates, enlarges, and reduces a prepared three-dimensional model having face part feature points so that the face part feature points most match face part feature points obtained from one camera, and (ii) calculates the face orientation based on the obtained rotation amount of the three-dimensional model.

Another example of the method for calculating the face orientation based on the positional relation of the face part feature points is a method which: (i) employs the principle of stereo disparity based on images captured by two cameras to calculate a three-dimensional position for each face part feature point out of a mismatch found on the images of positions of face part feature points in the right and left cameras; and (ii) calculates the face orientation based on the positional relation of the obtained face part feature points. Specifically, for example, there is a method which detects, as the face orientation, a direction of a normal line on a plane including three-dimensional coordinate points of a mouth and both eyes.

Now, description is continued with reference to the flowchart of FIG. 4.

The gaze direction detection unit 11 detects three-dimensional positions of inner corners of both eyes of the user using a stereo image captured by an image capturing device, and calculates a gaze direction reference plane using the detected three-dimensional positions of the inner corners of the both eyes (S506). After that, the gaze direction detection unit 11 detects the three-dimensional positions of the centers of the black parts of the both eyes of the user, using the stereo image captured by the image capturing device (S507). The gaze direction detection unit 11 then detects the black-part-of-the-eye direction, using the three-dimensional positions of the centers of the black parts of the both eyes and the gaze direction reference plane (S508).

Subsequently, the gaze direction detection unit 11 detects the gaze direction of the user, using the detected user's face orientation and the black-part-of-the-eye direction (S509).

Figure 6:
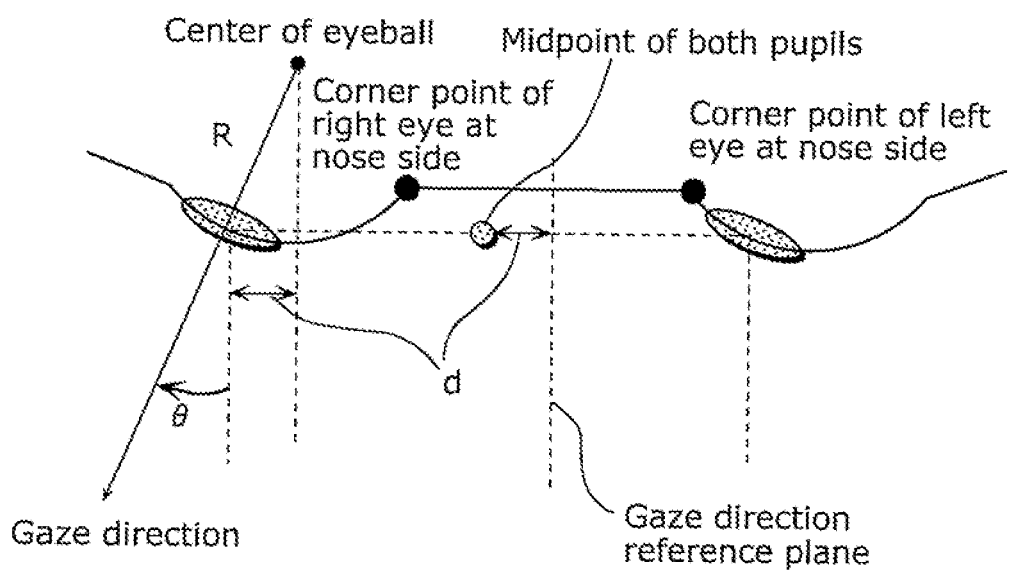
FIG. 6 is a diagram showing calculation of a gaze direction reference plane according to the embodiment of the present invention.
Figure 7:
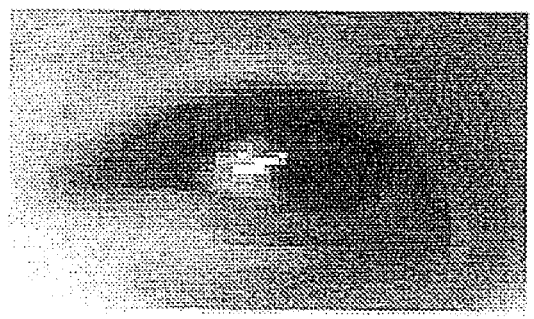
FIG. 7 is a diagram showing detection of the center of the black part of an eye according to the embodiment of the present invention.
Figure 8:
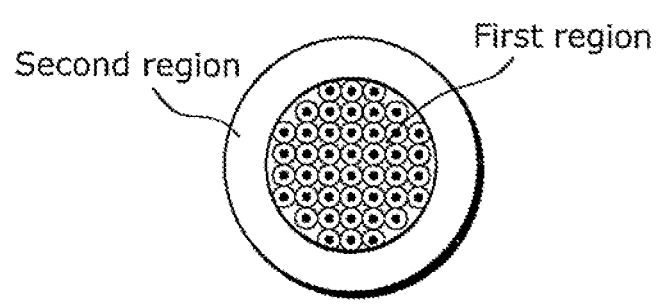
FIG. 8 is another diagram showing detection of the center of the black part of the eye according to the embodiment of the present invention.

Next, references are made to the details of the method for detecting the black-part-of-the-eye direction with reference to FIGS. 6 to 8.

In the present embodiment, the gaze direction detection unit 11 first calculates a gaze direction reference plane. The gaze direction detection unit 11 then detects the three-dimensional position of the center of the black part of the eye. Lastly, the gaze direction detection unit 11 detects the black-part-of-the-eye direction.

First, reference is made to the calculation of the gaze direction reference plane.

FIG. 6 is a diagram showing calculation of the gaze direction reference plane according to the embodiment of the present invention.

The gaze direction reference plane refers to a plane used as a reference in detecting the black-part-of-the eye direction, and is a bilateral symmetry plane of a face as shown in FIG. 6. The positions of the inner corners of the eyes move, depending on the facial expression, less than other face parts such as the tails of the eyes, corners of a mouth, or eyebrows; and thus cause fewer false detections. Thus, the gaze direction detection unit 11 calculates the gaze direction reference plane that is the bilateral symmetric plane of the face, using the three-dimensional positions of the inner corners of the eyes.

More particularly, the gaze direction detection unit 11 detects the inner corner regions of both eyes using a face detection module and a face part detection module for each of two images (stereo images) captured by a stereo camera that is an image capturing device. The gaze direction detection unit 11 then measures the three-dimensional positions of the inner corners of the both eyes, using a mismatch (disparity) between the images of the detected inner corner regions. Furthermore, as shown in FIG. 6, the gaze direction detection unit 11 calculates, as the gaze direction reference plane, the perpendicular bisector dividing a segment whose endpoints start at the three-dimensional positions of the inner corners of the both eyes.

Next, reference is made to the detection of the center of the black part of the eye.

FIG. 7 and FIG. 8 are diagrams showing the detection of the center of the black part of the eye according to the embodiment of the present invention.

People visually recognize an object when (i) a light from the object arrives at the retina via the pupil to be converted into an electric signal, and (ii) the electric signal is transmitted to the brain. Thus, the use of the position of the pupil allows detection of the gaze direction. However, irises of Japanese people's eye are black or blown. Thus, it is difficult to distinguish between a pupil and an iris through an image process. The center of the pupil approximately matches with the center of the black part of an eye (including both of the pupil and the iris). Hence, in the present embodiment, the gaze direction detection unit 11 detects the center of the black part of the eye when detecting the direction of the black part of the eye.

First, the gaze direction detection unit 11 detects the positions of the corner and the tail of an eye from a captured image. Then, the gaze direction detection unit 11 detects a region with little luminance from a region including the tail and the corner of the eye as shown in FIG. 7, as the black part of the eye region. Specifically, for example, the gaze direction detection unit 11 detects, as the black-part-of-the-eye region, a region whose (i) luminance is equal to or smaller than a predetermined threshold and (ii) size is greater than a predetermined size.

Next, the gaze direction detection unit 11 sets a black-part-of-the-eye detecting filter including a first region and a second region, as shown in FIG. 8, to any given position in the black-part-of-the eye region. Then, the gaze direction detection unit 11 (i) searches for a position, of the black-part-of-the-eye detecting filter, at which an inter-regional dispersion between the luminance of a pixel in the first region and the luminance of a pixel in the second region becomes the greatest, and (ii) detects the position indicated in the search result as the center of the black-part-of-the-eye. Similar to the above, the eye gaze direction detection unit 11 detects a three-dimensional position of the center of the black-part-of-the-eye, using a mismatch of the centers of the black-part-of-the-eyes in a stereo image.

Furthermore, reference is made to the detection of the black-part-of-the-eye direction.

The gaze direction detection unit 11 uses the calculated gaze direction reference plane and the detected three-dimensional position of the center of the black-part-of-the-eye to detect the black-part-of-the-eye direction. Adult eyeballs rarely vary in diameter from person to person. In the case of Japanese people, for example, the diameter is approximately 24 mm. Once position of the center of the black part of the eye is found when a user looks into a reference direction (front, for example), the gaze direction detection unit 11 obtains displacement from the center positions to current center positions of the black part of the eyes. Then, the eye gaze direction detecting unit 11 calculates to convert the obtained displacement into the black-part-of-the-eye direction.

When the user faces the front, the midpoint of the centers of the black parts of the both eyes is in the middle of the face, that is on the gaze direction reference plane. Using this, the gaze direction detection unit 11 calculates the distance between the midpoint of the centers of the black parts of the both eyes and the gaze direction reference plane to detect the black-part-of-the-eye direction.

Specifically, the gaze direction detection unit 11 uses the eyeball radius "R" and the distance "d" between the midpoint of the segment lying across the centers of the black parts of the both eyes and the gaze direction reference plane, to detect, as the black-part-of-the-eye direction, rotational angle θ in a horizontal direction with respect to a face orientation.

[Math 1]

$$\theta = \sin^{-1}\left(\frac{d}{R}\right) \quad (1)$$

As described above, the gaze direction detection unit 11 uses the gaze direction reference plane and three-dimensional positions of the centers of the black parts of both of the eyes to detect the black-part-of-the-eye direction. The gaze direction detection unit 11 then uses the detected user's face orientation and the detected black-part-of-the-eye direction to detect the gaze direction of the user in a real space.

Various types of methods are available for detecting the eye gaze direction, including a corneal reflex method, an electrooculography (EGO) method, a search coil method, and a scleral reflex method. Thus, the gaze direction detection unit 11 does not necessarily detect the eye gaze direction using the described method. For example, the gaze direction detection unit 11 may detect the gaze direction using the corneal reflex method.

The corneal reflex method measures eye movement based on a position of a corneal reflex image (purkinje image) that appears brightly when point light illumination is irradiated on a cornea. The center of eyeball rotation and the center of convex of a cornea do not match; and thus, when the cornea is regarded as a convex mirror and a reflection point of a light source is collected by a convex lens or the like, the collected point moves along the rotation of the eyeball. The eye movement is measured by capturing the point with an image capturing device.

Next, references are made in detail to the processing for detecting the event detection time from gaze trajectory (S104), the synchronization structure analysis processing (S105), and the gaze target determination processing (S106).

Figure 9A:
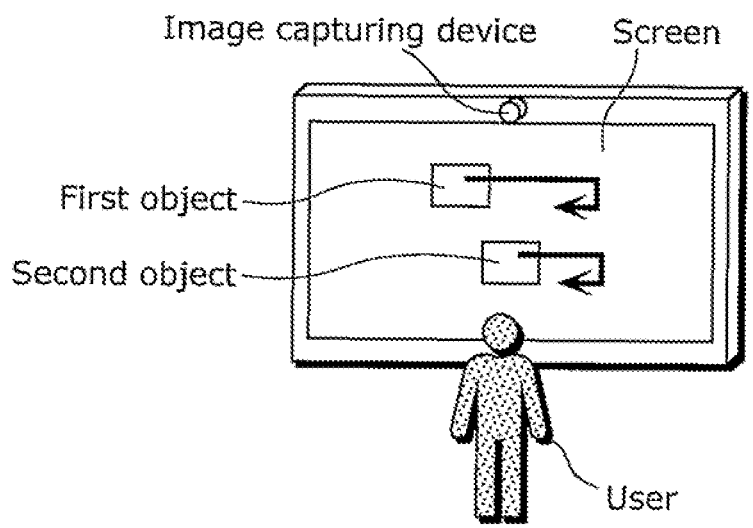
FIG. 9A is a diagram showing an arrangement example of objects displayed on a screen according to the embodiment of the present invention.
Figure 9B:
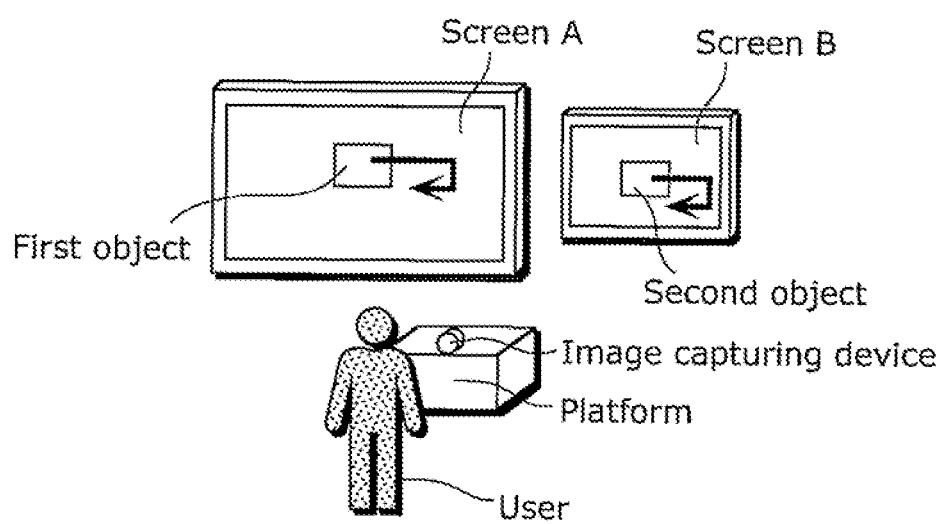
FIG. 9B is a diagram showing another arrangement example of objects displayed on a screen according to the embodiment of the present invention.

FIGS. 9A and 9B are diagrams each showing an arrangement example of objects displayed on a screen according to the present embodiment of the present invention.

As shown in FIGS. 9A and 9B, the gaze target determination device 10 according to the present embodiment determines the object at which a user is gazing from among a plurality of objects displayed on one or more screens. In other words, as shown in FIG. 9A, the gaze target determination device 10 determines the object at which the user is gazing from among objects displayed on a single screen. Or, as shown in FIG. 9B, the gaze target determination device 10 determines the object at which the user is gazing from among objects displayed on the screens (screen A and screen B).

In FIGS. 9A and 9B, a simplified case is shown where two objects are displayed on the screens and which of the objects is gazed at by the user is determined. First and second objects are arranged and displayed in the vertical direction, and they move only in the horizontal direction. This is because the detection accuracy of the gaze direction increases more in the movement in the horizontal direction than in the movement in the vertical direction.

As a matter of course, the number of objects, arrangement, and movement that are described here are only an example. More specifically, the number of objects may be two or more. Furthermore; the objects may be arranged and displayed, for example, in the horizontal or diagonal direction, or at random positions. In addition, the objects may move in the vertical or diagonal direction.

Figure 11:
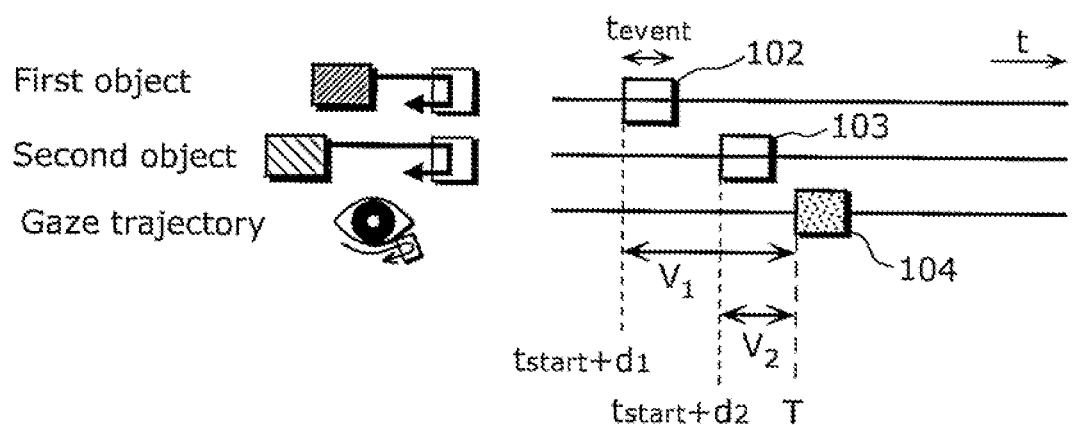
FIG. 11 is a diagram showing processing of synchronization structure analysis and gaze target determination according to the embodiment of the present invention.

FIG. 10 is a diagram showing processing for detecting event is detection time according to the embodiment of the present invention. FIG. 11 is a diagram showing processing of synchronization structure analysis and gaze target determination according to the embodiment of the present invention.

Here, it is assumed that the following expression represents the centroid position on a two-dimensional plane at time t of each of N objects which are included in the content displayed on a screen.

[Math2]

$$x_i(t) \ (i=1,\ldots,N, \ x_i \in \Re^2) \quad [\text{Math 2}]$$

Further, a case is assumed where the N objects move in the same way at a very small time difference. More specifically, the movement $x_i(t)$ of the i-th object in the horizontal direction is expressed as in the following equation 2 using a given continuous function x(t).

[Math 3]

$$x_i(t)=x(t+d_i)+b_i \ (x, b_i \in \Re^2) \quad (2)$$

Here, $d_i$ represents time difference between the movement of the i-th object $x_i(t)$ and x(t) and $b_i$ represents positional difference between the movement of the i-th object $x_i(t)$ and x(t).

It is preferable that the following points are considered when determining the movement x(t) of the object.
(1) Object Movement Area When an area where an object moves is very small, eye movement is also small. As a result, the eye movement may be buried in measurement errors of gaze direction detection. Thus, for example, if the gaze direction detection unit 11 has a detection error of, e.g. 50 mm, it is preferable to move objects in the range not less than 50 mm.

In other words, it is preferable that a display event triggers a movement of the gaze direction greater than an error in the gaze direction detection performed by the gaze direction detection unit 11. More specifically, it is preferable that a display event triggers a movement of the gaze position greater than an error in the gaze position caused due to an error in the gaze direction detection performed by the gaze direction detection unit 11. In other words, it is preferable that the event setting unit 13 moves each object more than the error in the gaze position caused due to the detection error of the gaze direction, so as to generate a display event.
(2) Moving Speed of Object Generally, it is said that the speed at which eye gaze can track an object that moves smoothly is 2 to 40 [degree/sec]. It is disclosed by Non-Patent Literature 2 (The Vision Society of Japan: "Handbook of Visual Information Processing", Asakura Publishing Company Ltd., 2000).

In view of these points, for example, a sine wave represented by the Equation (3) can be employed as the object movement $x_i(t)$.

[Math 4]

$$x_i(t) = a\sin\left(\frac{2\pi t}{T} + \theta_i\right) \quad (3)$$

Here, $\theta_i$ is a time difference represented as a phase difference between objects.

For example, when a user is positioned approximately 1 m in front of a 50-inch screen, an example of the setting may be that amplitude a=162.0 [mm], and period T=3.67 [sec].

In other words, in the present embodiment, the event setting unit 13 reciprocates objects in a horizontal direction. The event setting unit 13 does not necessarily reciprocate the objects in the horizontal direction, but may reciprocate the objects in a vertical or diagonal direction.

When $x_{gaze}(t)$ represents gaze coordinate series that are coordinate series of user's gaze positions on the screen calculated by the gaze trajectory calculation unit 12 based on the gaze direction detected by the gaze direction detection unit 11, and in the case where the user is gazing at an object, it is considered that $x_{gaze}(t)$ reflects the movement of the object at which the user is gazing. The gaze coordinate series correspond to the gaze trajectory.

Generally, in the gaze target determination which allows a user to take any postures or standing positions freely, $x_{gaze}(t)$ includes a relatively large measurement error. Therefore, the object's movement that is buried in the error cannot be detected from the eye movement of the user.

Thus, a characteristic movement of an object in a given time interval in the object movement x(t) is defined as a display event. Here, the display event trajectory e(t) relative to the object movement x(t) is represented by the Equation (4).

[Math 5]

$$e(t)=x(t+t_{start}) \quad (0 \le t \le t_{event}) \tag{4}$$

Here, $t_{start}$ represents event occurrence time and $t_{event}$ represents time length of the event occurrence interval.

As shown in FIG. 10(b), the event setting unit 13 generates the display event trajectory e(t) for each object in the time interval of $[t_{start}+d_i, t_{start}+d_i+t_{event}]$ (a first event occurrence interval 102 and a second event occurrence interval 103). Here, the time defined by $t_{start}+d_i$ is referred to as event occurrence time in each object. The display event triggers eye movement that is easily detected even when the measurement error of the eye movement is large. More specifically, a display event triggers a movement of a gaze position greater than an error in the gaze position caused due to an error in the gaze direction detection performed by the gaze direction detection unit 11.

Examples of a display event include a movement such as translational return. In other words, return movement is made by reciprocating an object in the horizontal direction and the movement around the return point is defined as a display event. Thus, the display event indicates a movement including a change in the moving direction. More specifically, the display event indicates a movement including a reverse in the moving direction.

When the user's eye tracks the display event, the gaze coordinate series $x_{gaze}(t)$ indicates characteristics similar to the display event trajectory e(t). Here, the gaze trajectory that is assumed to appear when the user's eye tracks an event is referred to as a gaze trajectory template. The eye movement event detection unit 14 obtains correlation between the gaze coordinate series $x_{gaze}(t)$ and the gaze trajectory template to extract the event detection interval 104 in the gaze coordinate series $x_{gaze}(t)$ as shown in FIG. 10(c). The eye movement event detection unit 14 then detects the start time of the extracted event detection interval 104 as the event detection time T at which the eye movement starts to track the display event of the gaze target. Hereinafter, the time T may be referred to as the event occurrence time in the eye movement.

Here, as shown in FIG. 10(a), the display event trajectory e(t) is used as the gaze trajectory template 101.

By doing so, the event occurrence time T in the eye movement can be obtained, as shown in the following equation (5), by calculating correlation degree between the gaze coordinate series $x_{gaze}(t)$ and the gaze trajectory template (event trajectory) e(t).

[Math 6]

$$T = \underset{t}{\mathrm{argmax}}(\mathrm{corr}(x_{gaze}(t), e(t))) \tag{5}$$

Here, corr is a normalized cross correlation function which is represented by the following equation (6).

[Math 7]

$$\mathrm{corr}(x_{gaze}(t), e(t)) = \frac{\int (x_{gaze}(m) - \bar{x}_{gaze})(e(t+m) - \bar{e})dm}{\sqrt{\int (x_{gaze}(m) - \bar{x}_{gaze})^2 dm} \sqrt{\int (e(t+m) - \bar{e})^2 dm}} \tag{6}$$

Here, the average values of the $x_{gaze}(t)$ and e(t) are indicated by the following expressions.

[Math 8]

$$\bar{x}_{gaze}, \bar{e}$$

In such a manner, the eye movement event detection unit 14 detects the event detection time based on the similarity between the movement trajectory indicated by the display event and the gaze trajectory. More specifically, the eye movement event detection unit 14 calculates, for each time interval of the gaze trajectory, a correlation degree indicating a similarity between the gaze trajectory and the movement trajectory indicated by the display event, to detect, as the event detection time, the start time of the time interval for which the correlation degree indicating the highest similarity is obtained.

As shown in FIG. 11, the synchronization structure analysis unit 15 analyzes the synchronization structure between the event occurrence time $t_{start}+d_i$ for each object and the event occurrence time T in the eye movement. In other words, the synchronization structure analysis unit 15 calculates, for each object, time difference between the event detection time T and the event occurrence time $t_{start}+d_i$.

The gaze target determination unit 16 then determines, based on the calculated time difference, the user's gaze target from among a plurality of objects.

Here, for each object, an evaluation value $V_i$ is used for determining whether an object is the gaze target of the user. If the user's eye tracks the movement of an object, it is considered that the event occurrence time of the object synchronizes with the event occurrence time in the eye movement. Therefore, using the time difference between the event occurrence time $t_{start}+d_i$ in each object and the event occurrence time T in the eye movement, the evaluation value $V_i$ is defined as in the following equation (7). More specifically, the synchronization structure analysis unit 15 calculates, for each object, the time difference between the event detection time T and the event occurrence time $t_{start}+d_i$ as the evaluation value $V_i$.

[Math 9]

$$V_i = T - (t_{start}+d_i) \tag{7}$$

For example, in FIG. 11, the synchronization structure analysis unit 15 calculates, as the evaluation value $V_1$, the time difference between the event detection time T and the event occurrence time $t_{start}+d_1$ of a first object. Further, the synchronization structure analysis unit 15 calculates, as the evaluation value $V_2$, the time difference between the event detection time T and the event is occurrence time $t_{start}+d_2$ of a second object.

Here, assumed a case where the user keeps gazing at one object for a predetermined time without changing the gaze target on the screen. In this case, it is sufficient that the event setting unit 13 moves objects so that a display event occurs once for each object during the time interval in which the gaze target determination is performed. The synchronization structure analysis unit 15 compares the evaluation value $V_1$ of each object to determine synchronization degree indicating the degree of synchronization between the display event for each object and eye gaze (eye movement) to the display event.

Here, if a k-th object is the gaze target, the evaluation value $V_k$ is smaller than the evaluation values of other objects. In other words, if the k-th object is the gaze target, the following equation (8) is established.

[Math 10]

$$k = \underset{i}{\mathrm{argmin}} |V_i| \quad (8)$$

Thus, the gaze target determination unit 16 is capable of determining, based on the equation (8), that the k-th object has the highest gaze synchronization degree. As a result, the k-th object can be determined as the gaze target of the user.

More specifically, the gaze target determination unit 16 determines the object for which the smallest time difference is calculated, as the object at which the user is gazing. For example, in FIG. 11, the gaze target determination unit 16 determines the second object as the gaze target, because the evaluation value $V_2$ indicating the time difference of the second object is smaller than the evaluation value $V_1$ indicating the time difference of the first object.

In such a manner, the gaze target determination device 10 according to the present embodiment detects, as the event detection time, the start time of the time interval which is highly correlated with the gaze trajectory template which is in advance associated with the display event, based on the gaze trajectory calculated when a predetermined event is generated at different times to each object on the screen. Furthermore, the gaze target determination device 10 determines the gaze target of the user, based on the time difference between the event occurrence time of each object and the event detection time. Therefore, it is possible to accurately determine the gaze target of the user from among a plurality of objects on the screen.

In other words, the gaze target determination device 10 can determine the gaze target of the user based on the time difference between the event detection time and the event occurrence time; and thus, it is possible to accurately determine the object at which the user is gazing from among a plurality of objects displayed on the screen.

Furthermore, it is sufficient that the gaze target determination device 10 generates a display event at different times for each of the objects; and thus, it is possible to generate the same display event for the objects. Therefore, the gaze target determination device 10 can determine the gaze target while the objects displayed on the screen move in a harmonious way.

Further, the gaze target determination device 10 determines the gaze target based on, not the gaze position, but the movement of the gaze direction; and thus, it is possible to accurately determine the gaze target even when the detection accuracy of the gaze direction is low. More specifically, the gaze target determination device 10 is capable of determining the gaze target, for example, based on the movement trajectory of the object and the movement trajectory of the gaze position; and thus, it is possible to accurately determine the gaze object even when the detection accuracy of the gaze direction is low.

The gaze target determination device 10 also determines the gaze target based on the display event which triggers the gaze direction movement greater than the detection error of the gaze direction. Thus, the gaze target determination device 10 can reduce the false determination of the gaze target caused due to the error in the gaze detection; and thus, it is possible to determine the gaze target with higher accuracy.

Using characteristics of human eyes that the eye gaze movement in the horizontal direction can be more easily detected than the movement in the vertical direction, the gaze target determination device 10 is also capable of determining the gaze target with higher accuracy by generating movement of objects in the horizontal direction as display events.

Using the fact that the gaze target is accurately determined, the gaze target determination device 10 is also capable of creating, for example, database used for estimating user's preference. The gaze target determination device 10 is also capable of increasing user's convenience by, for example, further displaying information and the like regarding the target object that is accurately determined.

In the present embodiment, the gaze direction detection unit 11 detects the gaze direction using a three-dimensional eyeball model or the like, from an image of a user captured by a camera, assuming that the three-dimensional vector connecting the center of the eyeball and the center of the iris is the gaze direction. However, the gaze direction detection unit 11 may, of course, detect the gaze direction using a method such as a pupil-corneal reflex method which irradiates near-infrared light onto an eye using an LED to estimate the gaze direction based on the positions of the light source image (Purkinje image) reflected on the cornea and the pupil.

In addition, in the present embodiment, the event detection time is the start time of the event detection interval; however, it is not necessarily always so. For example, the event detection time may be a median value of an event detected interval. In this case, the event occurrence time is also a median value of the event occurrence interval.

Furthermore, in the present embodiment, the event setting unit 13 generates the same display event for all of the objects; however, the event setting unit 13 does not necessarily generate the same display event for all of the objects. For example, it may be that the event setting unit 13 generates the first display event for the first and second objects at different times, and generate the second display event different from the first display event for third and fourth objects at different times. In this case, too, the gaze target determination device 10 is capable of accurately determining the gaze target.

In the present embodiment, a case has been described where gaze trajectory is gaze coordinate series; however, the gaze trajectory is not necessarily the gaze coordinate series. In other words, it is sufficient that the gaze trajectory indicates the gaze direction movement, and not necessarily indicate the movement of the gaze position. For example, in the case where the user's head hardly moves (the movement is negligible), the gaze trajectory may be the movement trajectory of the center position of the black part of the eye. In this case, too, the eye movement event detection unit 14 is capable of detecting, as the event detection time, the time at which the center position of the black part of the eye moves according to the display event. More specifically, the gaze target determination device can determine the gaze target using the movement of the gaze direction, but not using the gaze position; and thus, it is possible to accurately determine the gaze target. In the case where the user moves his or her head to some extent, it is preferable that the gaze trajectory is gaze coordinate series that reflects the influences of both the eye movement and the head movement.

The gaze target determination device according to one aspect of the present invention has been described based on the embodiment; however, the present invention is not limited to the embodiment. Those skilled in the art will readily appreciate that many modifications are possible in the exemplary embodiment without materially departing from the novel teachings and advantages of this invention, and therefore, all such modifications are intended to be included within the scope of this invention. Hereinafter, references are made to various variations of the embodiment.

(Variation 1)

Hereinafter, reference is made to Variation 1 of the embodiment of the present invention.

In the embodiment, the gaze target determination unit 16 determines the object for which the smallest time difference is calculated, as the object at which the user is gazing. However, as disclosed in Non-Patent Literature 2 (The Vision Society of Japan: "Handbook of Visual Information Processing", Asakura Publishing Company Ltd., 2000), latent time that is time period required before the eye starts tracking the movement of an object in a smooth eye movement is generally 60 to 150 ms.

In other words, the time difference between the event occurrence time and the event detection time is less than the latent time, the user is less likely to be gazing at the object for which a display event is generated at the event occurrence time. As described below, the gaze target determination unit 16 according to the Variation 1 determines, as the gaze target, only the object which has time difference that is equal to or greater than the latent time, when determining the gaze target using the evaluation value $V_i$.

The differences between the gaze target determination device 10 according to the Variation 1 and that in the embodiment are mainly described in the following.

Figure 12:
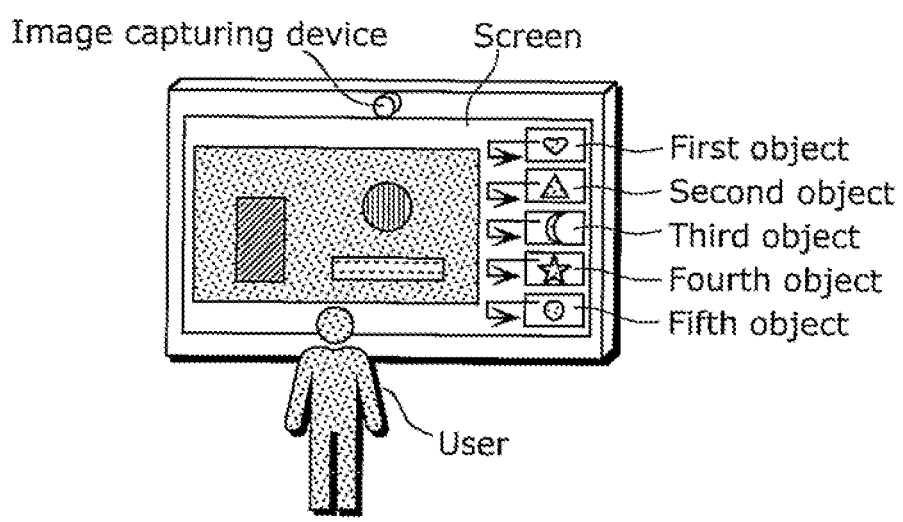
FIG. 12 is a diagram showing an arrangement example of objects according to Variation 1 of the embodiment of the present invention.

FIG. 12 is a diagram showing an arrangement example of objects according to the Variation 1 of the embodiment of the present invention.

As shown in FIG. 12, even in the case where content such as a video is displayed on an area, of the screen, greater than half of the size of the screen and where objects are displayed such as recommended information or notification to the user are displayed near the area, the gaze target determination device 10 according to the Variation 1 can determine the gaze target.

Figure 13:
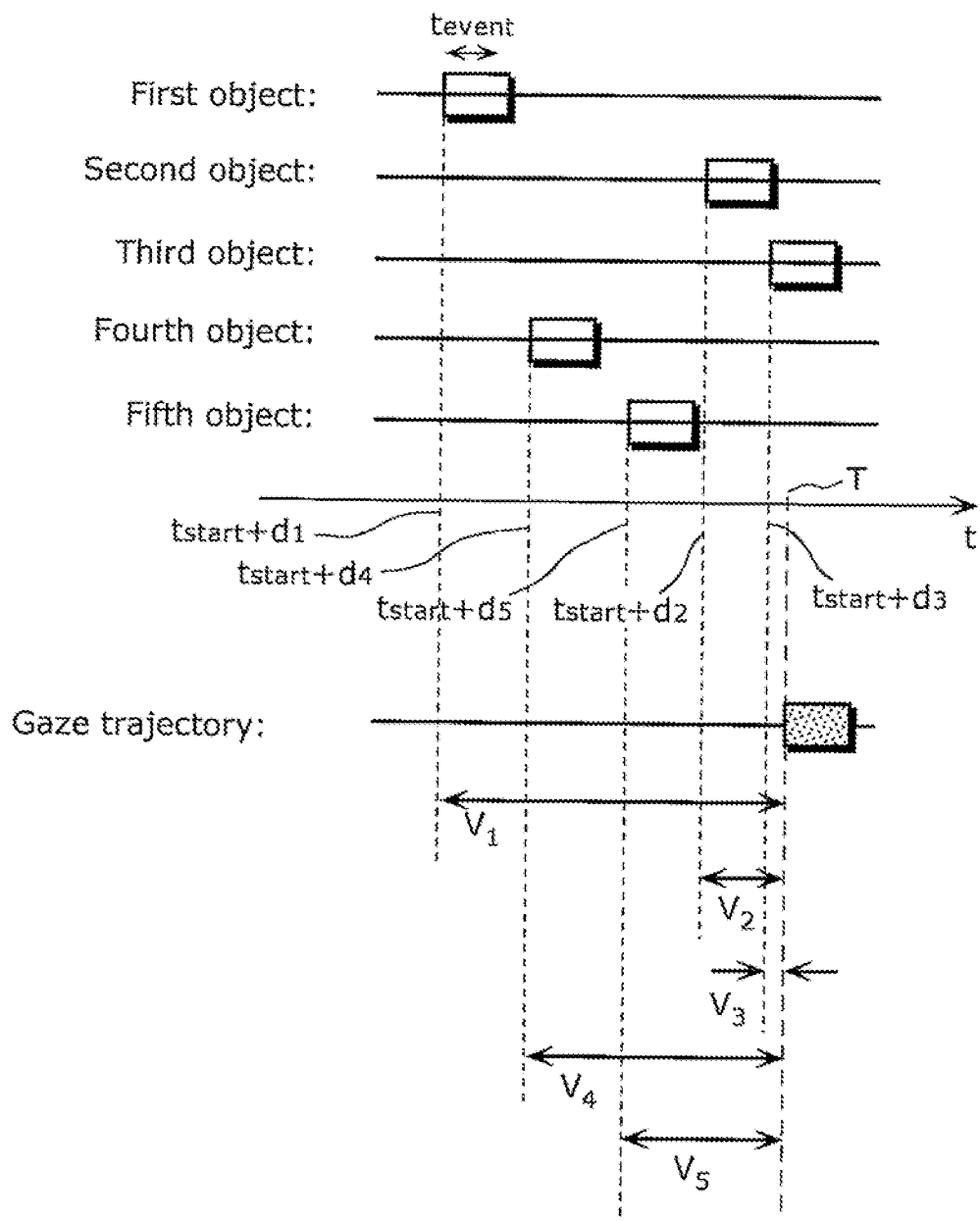
FIG. 13 is a diagram showing processing of synchronization structure analysis and gaze target .determination according to the Variation 1 of the embodiment of the present invention.

FIG. 13 is a diagram showing processing of synchronization structure analysis and gaze target determination according to the Variation 1 of the embodiment of the present invention. More particularly, FIG. 13 is a diagram for showing the method for analyzing synchronization structure between display events and eye movement when there are five objects.

In FIG. 13, the event setting unit 13 generates display events for first to fifth objects at event occurrence times $t_{start}+d_1$ to $t_{start}+d_5$. The eye movement event detection unit 14 detects the event detection time T from the gaze trajectory.

In such a condition, when the evaluation values $V_1$ to $V_5$ are calculated for the first to fifth objects, in the above embodiment, the gaze target determination unit 16 determines, as the gaze target, the third object which has the evaluation value smaller than the evaluation values of other objects.

However, as described earlier, it is generally considered that the latent time required before the eye starts tracking the movement of the target in a smooth eye movement is 60 to 150 ms. Thus, the gaze target determination unit 16 needs to exclude $V_k$ that is smaller than the latent time from the determination of the gaze target.

Accordingly, for example, in FIG. 13, when the latent time required before the eye starts to track the movement of the object is 60 ms, and the evaluation value $V_3$ is less than 60 ms, the gaze target determination unit 16 needs to obtain the smallest value among the evaluation values $V_1$ to $V_5$ while excluding the evaluation value $V_3$. In this case, the evaluation value $V_2$ is the smallest value; and thus, the gaze target determination unit 16 determines the second object as the gaze target. If the evaluation value $V_3$ is equal to or greater than 60 ms, it is sufficient that the gaze target determination unit 16 determines the third object as the gaze target.

In such a manner, the gaze target determination unit 16 determines, as the object at which the use is gazing, the object for which the time difference which is equal to or greater than the reference time difference and is closest to the reference time difference is calculated. In other words, the gaze target determination unit 16 determines, as the object at which the user is gazing, the object for which the smallest time difference is calculated, while excluding the objects for which the time difference less than the reference time difference is calculated.

Here, it is sufficient that the reference time difference is determined based on the latent time. For example, it is sufficient that the reference time difference is the same as the latent time as described above. The reference time difference may also be the time difference obtained by adding the value, taking the error in the gaze detection or the like into account, to the latent time, or subtracting the value from the latent time.

As described, the gaze target determination device 10 according to the Variation 1 can exclude the determination of, as the gaze target, the object for which the time difference which is less than the latent time that is required before the eye starts to track the movement of the object in a smooth eye movement is detected. As a result, the gaze target determination device 10 is capable of determining the gaze target with higher accuracy.

Further, the gaze target determination device 10 is capable of improving temporal resolution of the gaze target determination, because $d_i$ and $t_{event}$ that are defined for each object can be decreased. More specifically, the gaze target determination device 10 can accurately determine the gaze target even when a display event for each object is generated at a shorter time interval. As a result, the gaze target determination device 10 can increase flexibility in the display event occurrence method for each object; and thus, it is possible to reduce the feeling of strangeness experienced by the user and to generate display events for a plurality of objects in a harmonious way.

(Variation 2)

Next, reference is made to Variation 2 of the embodiment of the present invention.

In the embodiment, the display event triggers, for the user who is gazing a t an object, the movement of the gaze position which takes the movement trajectory similar to that of the object. However, in the Variation 2, a display event triggers, for the user who is gazing at an object, the movement of the gaze position at a speed equal to or higher than a predetermined speed.

The differences between the gaze target determination device 10 according to the Variation 2 and that in the embodiment are mainly described in the following.

As described earlier, in the Variation 2, a display event triggers, for the user who is gazing at an object, the movement of the gaze position at a speed equal to or higher than a predetermined speed. More specifically, for the user who is gazing at a character string to read the character sting included in an object, the display event triggers the movement of the gaze position at a speed equal to or higher than a predetermined speed. More particularly, the display event indicates a change of an initial character included in the character string from an unreadable state to a readable state.

The event setting unit 13 generates a display event by changing characters included in a character string in an object from an unreadable state to a readable state. More specifically, the event setting unit 13 generates a display event by changing the characters included in the character string from a readable state to an unreadable state, and then changing the initial character in the character string from the unreadable state to the readable state.

Here, the unreadable state refers to a display state where the user is not able to read characters. Typically, the unreadable state is a state where characters are not being displayed. Examples of the unreadable state also include a state where clarity of characters is less than a predetermined threshold, and a state where the size of the characters is less than a predetermined size. Here, clarity refers to clarity of the characters. For example, if pixelization is performed on characters, clarity is low. It is sufficient to use, for the predetermined threshold or the predetermined size, boundary value of clarity or character size which does not allow the user to read the characters displayed on the screen and which is obtained based on experiments or experiences.

The readable state refers to a state where the user can read characters. For example, the readable state refers to a state where characters are displayed and clarity of the characters is equal to or greater than a predetermined threshold, or the size of the characters is equal to or greater than a predetermined size.

The eye movement event detection unit 14 detects, as the event detection time, the time at which the gaze position moves at a speed equal to or higher than a predetermined speed, based on the gaze trajectory calculated by the gaze trajectory calculation unit 12. More particularly, the eye movement event detection unit 14 detects, as the event detection time, for example, the start time of the event detection interval during which the moving speed of the gaze position is equal to or higher than a predetermined speed over a predetermined time.

Figure 14:
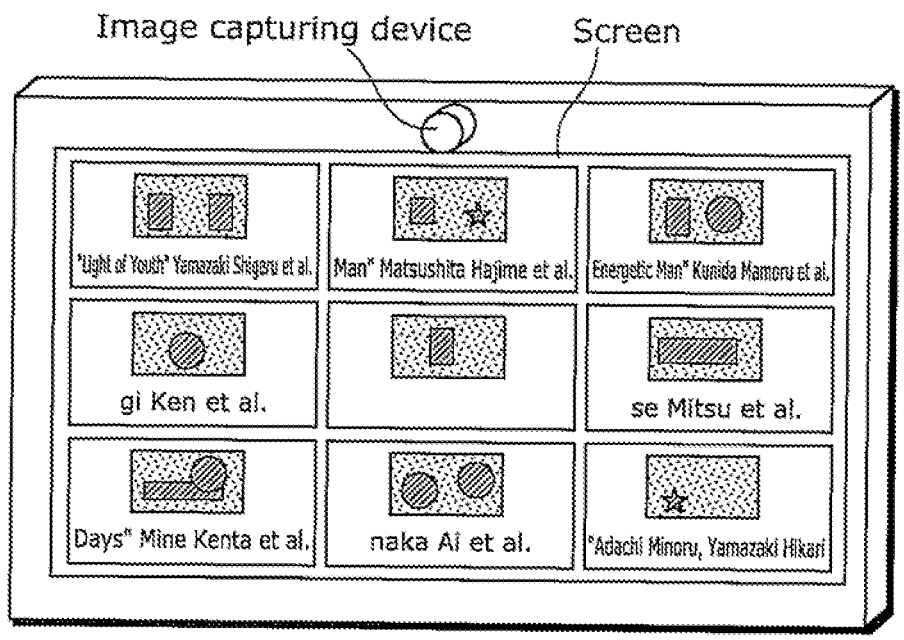
FIG. 14 is a diagram showing an arrangement example of objects displayed on a screen according to Variation 2 of the embodiment of the present invention.
Figure 15:
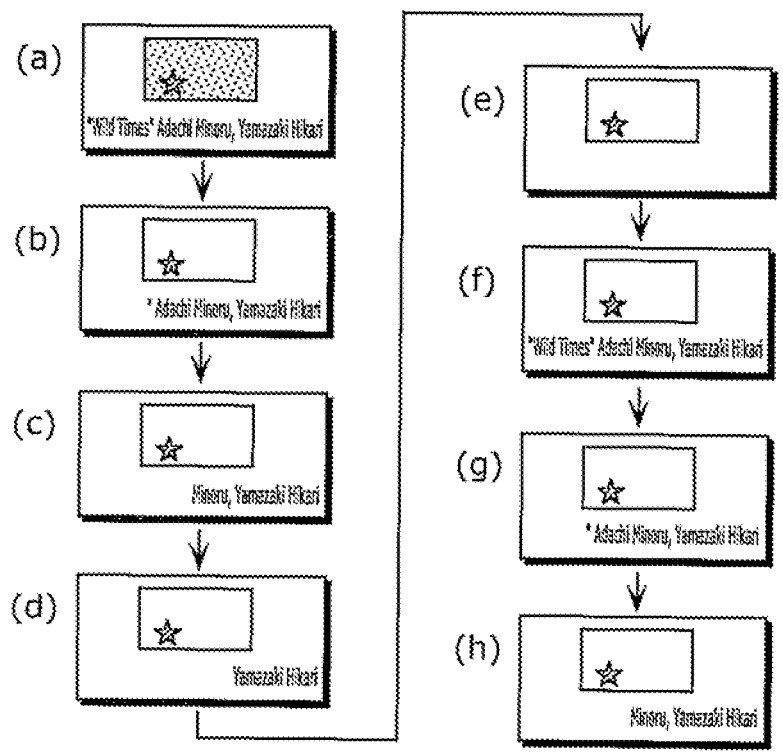
FIG. 15 is a diagram showing an example of a display event according to the Variation 2 of the embodiment of the present invention.

Next, reference is made to specific examples of the display event according to the Variation 2, with reference to FIG. 14 and FIG. 15

FIG. 14 is a diagram showing an arrangement example of objects displayed on a screen according to the Variation 2 of the embodiment of the present invention. As shown in FIG. 14, there are nine objects on the screen. The respective objects include a thumbnail image of video and a character string (hereinafter, may be referred to as "text") representing the content of the video.

FIG. 15 is a diagram showing an example of a display event according to the Variation 2 of the embodiment of the present invention. More particularly, FIG. 15 is a diagram showing change over time of one object displayed on a screen.

As shown in FIG. 15(*a*) to (*h*), text sequentially fades out from the left most character. More specifically, the event setting unit 13 changes the characters included in the text from the readable state to the unreadable state in reading order. Thus, the user always reads the part immediately to the right of the faded out portion.

In the case where the object is an image, the position within the object and the order the gaze is directed to depends on conditions and person. However, in the case where the object includes text, the user is basically needs to read the characters in reading order by directing the gaze from the beginning of a word to the end of the word, and from the beginning of a sentence to the end of the sentence so that the user can understand the content of the text.

Thus, if the user continues reading the text to understand the content of the text, in FIG. 15(*d*) to (*f*), the gaze movement of the user indicates characteristic movements compared to other cases. In other words, the user needs to move the gaze position quickly to read the text in FIG. 15(*d*) to (*f*).

In the Variation 2, as shown in FIG. 15(*d*) to (*f*), such a display event is used where the initial character included in the text is changed from the unreadable state to the readable state. More specifically, in the Variation 2, the change in the display state of the characters which triggers the movement of the gaze position of the user at a speed equal to or higher than a predetermined speed is used as a display event.

The event setting unit 13 generates display events such that the time at which the display events are generated (event occurrence time) are different among nine objects displayed on the screen.

By doing so, the eye movement event detection unit 14 extracts the time interval during which the moving speed of the gaze position is equal to or higher than a predetermined speed, as the event detection interval from the gaze coordinate series $x_{gaze}(t)$ calculated by the gaze trajectory calculation unit 12. The eye movement event detection unit 14 then detects, as the event occurrence time, the start time of the extracted event detection interval.

In addition, similar to the embodiment, the synchronization structure analysis unit 15 calculates the time difference between the event detection time and the event occurrence time of each object. As a result, the gaze target determination unit 16 is capable of determining the object for which the smallest time difference is calculated, as the gaze target.

In such a manner, the gaze target determination device 10 according to the Variation 2 is capable of determining the gaze target based on the moving speed of the gaze position; and thus, it is possible to accurately determine the gaze target even when the detection accuracy of the gaze direction is low.

Furthermore, the gaze target determination device 10 can accurately determine the gaze target of the user who is gazing at the object to read the character string.

The gaze target determination device 10 can also generate a display event while reducing the feeling of strangeness experienced by the user who is gazing at the object to read the character string.

(Variation 3)

Next, reference is made to Variation 3 of the embodiment of the present invention.

In the Variation 3, similar to the Variation 2, a display event trigger, for the user who Is gazing at an object to read a character string, the movement of the gaze position at a speed equal to or higher than a predetermined speed. However, the event setting unit 13 according to the Variation 3 triggers a display event different from that in the Variation 2.

Hereinafter, the differences between the gaze target determination device 10 according to the Variation 3 and that of the Variation 2 are mainly described.

In the Variation 3, the event setting unit 13 generates a display event by (i) changing, in reading order, characters included in a character string from the unreadable state to the readable state, and further changing, in the reading order, the characters that are in the readable state to be in the unreadable state, and (ii) changing the initial character included in the character string from the unreadable state to the readable state.

In the following, specific examples of display events according to the Variation 3 are described with reference to FIG. 16 and FIG. 17.

Figure 16:
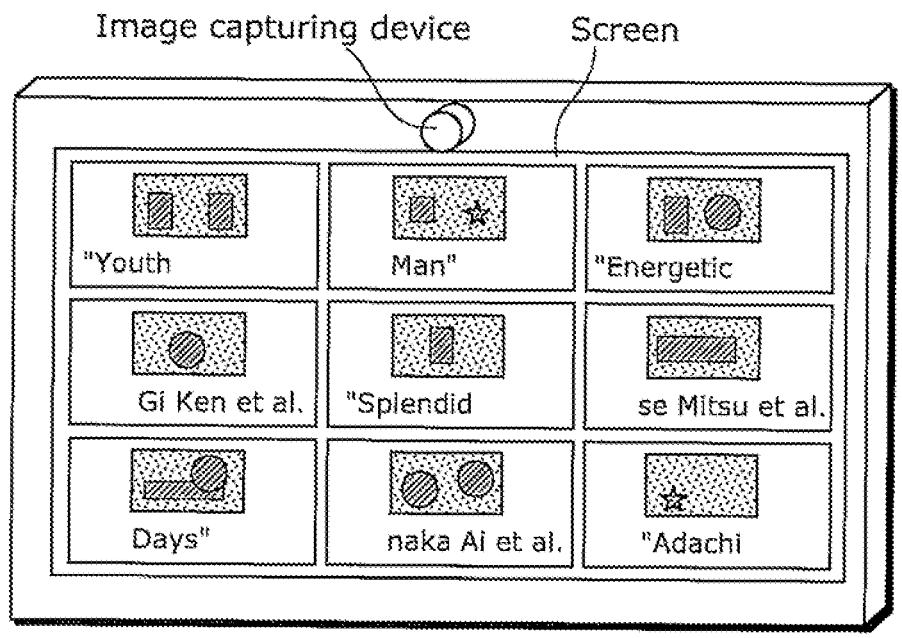
FIG. 16 is a diagram showing an arrangement example of objects displayed on a screen according to Variation 3 of the embodiment of the present invention.

FIG. 16 is a diagram showing an arrangement example of objects displayed on a screen according to the Variation 3 of the embodiment of the present invention. The arrangement of the objects displayed on the screen is the same as that in FIG. 14; and thus, its description is not repeated.

Figure 17:
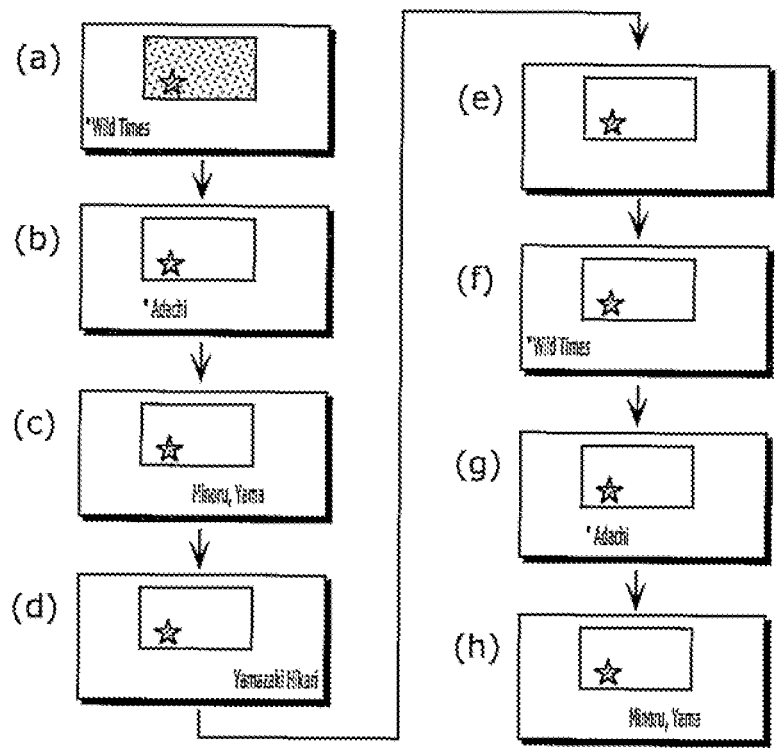
FIG. 17 is a diagram showing an example of a display event according to the Variation 3 of the embodiment of the present invention.

FIG. 17 is a diagram showing an example of a display event according to the Variation 3 of the embodiment of the present invention. More particularly, FIG. 17 is a diagram showing change over time of one object displayed on a screen.

As shown in FIG. 17(a) to (h), only part of the text is displayed to the user in such a manner as if a spotlight is seemingly sequentially turned on and off from left to right along the line to be displayed. In other words, the event setting unit 13 changes characters included in a character string from the unreadable state to the readable state, and changes the characters from the readable state to the unreadable state in reading order.

In this case, the user always reads the character on which a spotlight is turned on. Thus, in FIG. 17(d) to (f), the user quickly moves the gaze position from the right end to the left end.

In the Variation 3, as shown in FIG. 17(d) to (f), such a display event is used where the initial character included in the text is changed from the unreadable state to the readable state. More specifically, in the Variation 3, the change in the display state of the characters which triggers the movement of the gaze position of the user at a speed equal to or higher than a predetermined speed is used as a display event.

In such a manner, the gaze target determination device 10 according to the Variation 3 is capable of producing the advantageous effects similar to those of the gaze target determination device 10 according to the Variation 2.

(Variation 4)

Next, reference is made to Variation 4 of the embodiment of the present invention.

In the Variation 4, similar to the Variation 2, a display event triggers, for the user who is gazing at an object to read a character string, the movement of the gaze position at a speed equal to or higher than a predetermined speed. However, the display event according to the Variation 4 indicates such a change that character-spacing increases in a character string, which is different from the Variation 2.

Hereinafter, the differences between the gaze target determination device 10 according to the Variation 4 and that of the Variation 2 are mainly described.

As described, in the Variation 4, the display event indicates a change in which character-spacing increases in a character string.

The event setting unit 13 generates the display event by (i) moving a character string in one direction so as to pass through the object, and (ii) changing the character-spacing in the character string so that the character-spacing is larger than an immediately preceding character-spacing.

In the following, specific examples of display events according to the Variation 4 are described with reference to FIG. 18 and FIG. 19.

Figure 18:
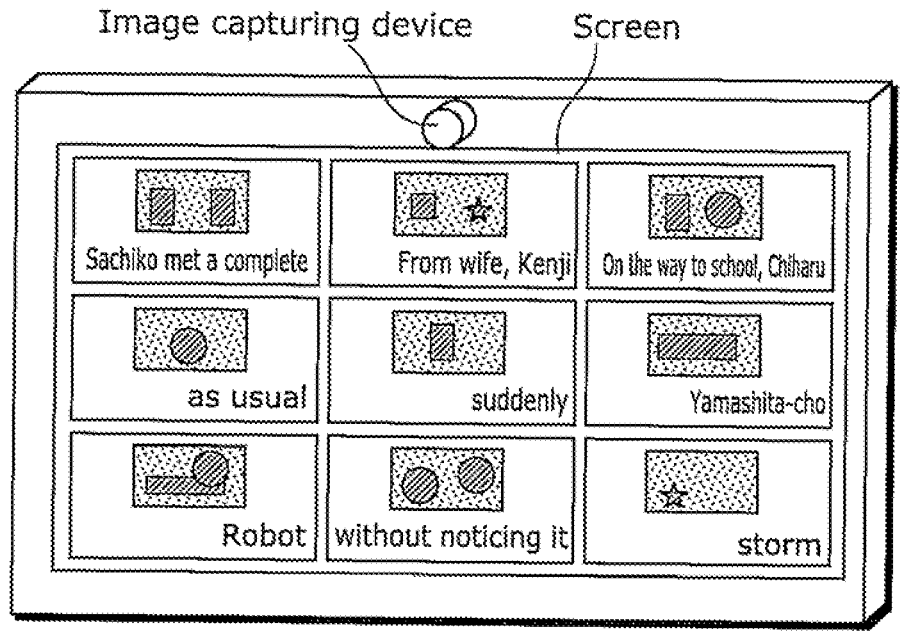
FIG. 18 is a diagram showing an arrangement example of objects displayed on a screen according to Variation 4 of the embodiment of the present invention.

FIG. 18 is a diagram showing an arrangement example of objects displayed on a screen according to the Variation 4 of the embodiment of the present invention. The arrangement of the objects displayed on the screen is the same as that in FIG. 14; and thus, its description is not repeated.

Figure 19:
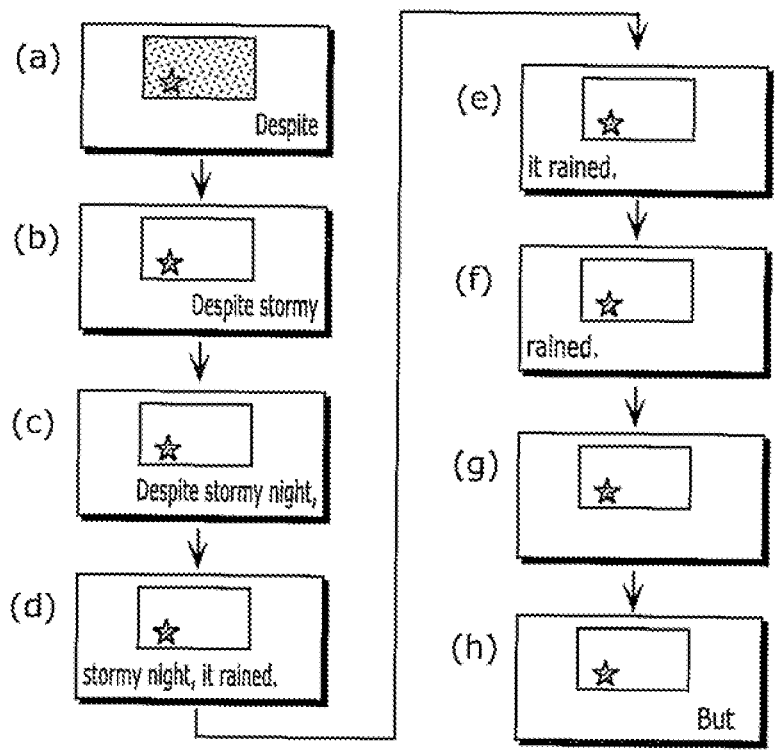
FIG. 19 is a diagram showing an example of a display event according to the Variation 4 of the embodiment of the present invention.

FIG. 19 is a diagram showing an example of a display event according to the variation 4 of the embodiment of the present invention. More particularly, FIG. 19 is a diagram showing change over time of one object displayed on a screen.

As shown in FIG. 19(a) to (h), text is displayed scrolling from right to left. In other words, the text moves in one direction so as to pass through the region where an object is displayed.

In this case, the user reads the characters that are passing through the region, in reading order. Thus, in FIG. 19(g) to (h), the user quickly moves the gaze position from the left end to the right end. In other words, the user needs to move the gaze positions markedly because the character-spacing is large.

In the Variation 4, as shown in FIG. 19(g) to (h), the change in which character-spacing increases is used as a display event. More specifically, in the Variation 4, the change in the character-spacing which triggers the movement of the gaze position of the user at a speed equal to or higher than a predetermined speed is used as a display event.

In such a manner, the gaze target determination device 10 according to the Variation 4 is capable of producing the advantageous effects similar to those of the gaze target determination device 10 according to the Variation 2.

(Variation 5)

Next, reference is made to Variation 5 of the embodiment of the present invention.

In the Variation 5, similar to the Variation 2, a display event triggers, for the user who is gazing at an object to read a character string, the movement of the gaze position at a speed equal to or higher than a predetermined speed. However, unlike the Variation 2, the display event according to the Variation 5 indicates, in a character string of multiple lines, a change of an initial character in a line from the unreadable state to the readable state.

Hereinafter, the differences between the gaze target determination device 10 according to the Variation 5 and that of the Variation 2 are mainly described.

As described, in the Variation 5, the display event indicates a change of an initial character in a line included in a character string from the unreadable state to the readable state.

The event setting unit 13 generates a display event by changing, in reading order, characters included in a character string in multiple lines from the unreadable state to the readable state.

In the following, specific examples of display events according to the Variation 5 are described with reference to FIG. 20 and FIG. 21.

FIG. 20 is a diagram showing an arrangement example of objects displayed on a screen according to the Variation 5 of the embodiment of the present invention. As shown in FIG. 20, in the Variation 5, three objects each including a character string of multiple lines are displayed on a screen.

FIG. 21 is a diagram showing an example of a display event according to the Variation 5 of the embodiment of the present invention. More particularly, FIG. 21 is a diagram showing change over time of one object displayed on a screen.

As shown in FIG. 21(a) to (c), the character string of multiple lines is displayed line by line in reading order. More specifically, the character string changes from the unreadable state to the readable state line by line in reading order.

In this case, the user reads the initial character of the newly displayed line after reading last character of the preceding line; and thus, the user needs to move the gazing point markedly from the right end to the left end of the object.

In the Variation 5, as shown in FIG. 21(a) to (c), the change of the initial character in the line from the unreadable state to the readable state is used as a display event. In other words, in the Variation 5, the change of the initial character in the line from the unreadable state to the readable state which triggers the movement of the gaze position of the user at a speed higher than a predetermined speed, is used as a display event.

In such a manner, the gaze target determination device 10 according to the Variation 5 is capable of producing the advantageous effects similar to those of the gaze target determination device 10 according to the Variation 2.

The event setting unit 13 displays a character string of multiple lines line by line in reading order, but does not always have to display the text line by line. For example, the event setting unit 13 may display the character string in multiple lines at once. Furthermore, for example, the event setting unit 13 may also display the character string by displaying characters singly or by multiple characters together.

(Variation 6)

Next, reference is made to Variation 6 of the embodiment of the present invention.

In the Variation 6, similar to the Variation 2, a display event triggers, for the user who is gazing at an object, the movement of the gaze position at a speed equal to or higher than a predetermined speed. However, the display event according to the Variation 6 can trigger the movement of the gaze position at a speed equal to or higher than a predetermined speed even when an object does not include a character string.

The differences between the gaze target determination device 10 according to the Variation 6 and that in the Variation 2 are mainly described in the following.

In the Variation 6, the event setting unit 13 generates display events by moving objects at a speed equal to or higher than a predetermined speed. More specifically, the event setting unit 13 moves each of objects at a speed equal to or higher than a predetermined speed at different times.

In the following, specific examples of display events according to the Variation 5 are described with reference to FIG. 22 and FIG. 23.

Figure 22:
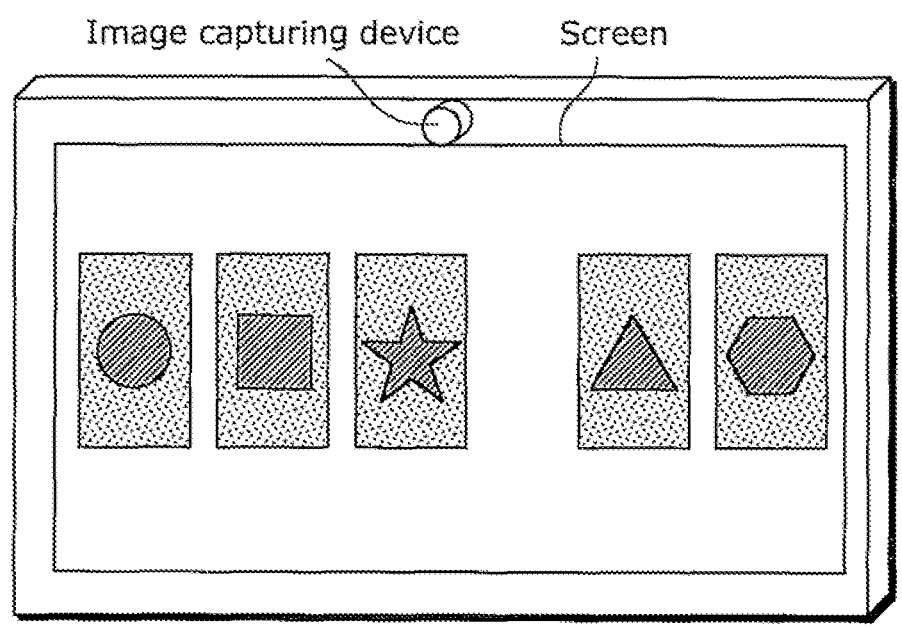
FIG. 22 is a diagram showing an arrangement example of objects displayed on a screen according to Variation 6 of the embodiment of the present invention.

FIG. 22 is a diagram showing an arrangement example of objects displayed on a screen according to Variation 6 of the embodiment of the present invention. As shown in FIG. 22, in the Variation 6, five objects are arranged in the horizontal direction on the screen.

Figure 23:
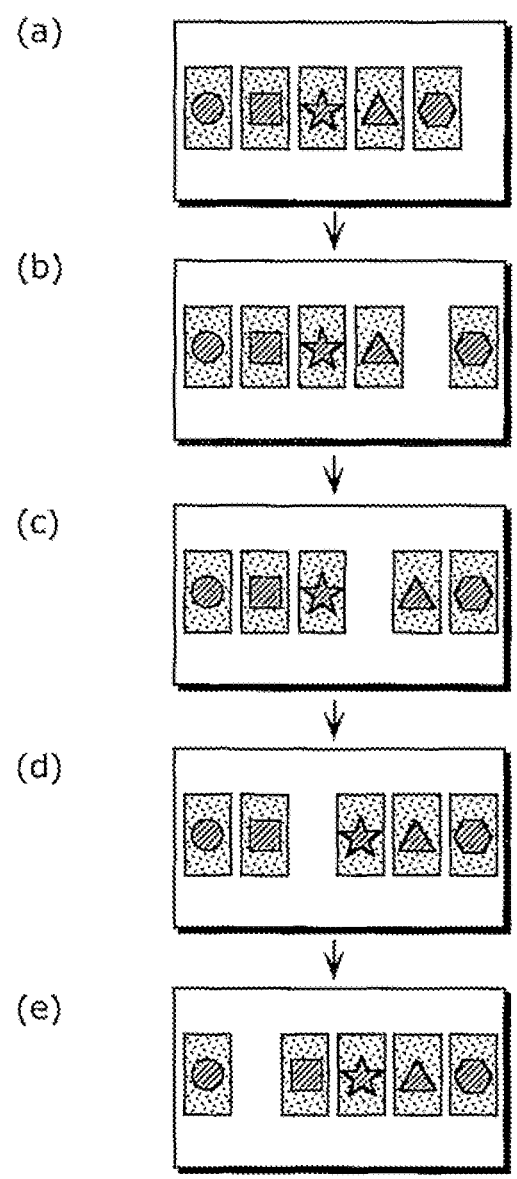
FIG. 23 is a diagram showing an example of a display event according to the Variation 6 of the embodiment of the present invention.

FIG. 23 is a diagram showing an example of a display event according to the variation 6 of the embodiment of the present invention. More particularly, FIG. 23 is a diagram showing change over time of five objects displayed on a screen.

As shown in FIG. 23(*a*) to (*e*), each object sequentially moves to the right at a speed equal to or higher than a predetermined speed. More specifically, the event setting unit 13 moves an object at a speed equal to or higher than a predetermined speed after a preceding object in the moving direction is moved.

In this case, when the object at which the user is gazing moves, the user moves the gaze position at a speed similar to that of the object.

Thus, the eye movement event detection unit 14 detects, as the event detection time, time at which the gaze position moves at a speed equal to or higher than a predetermined speed.

In such a manner, the gaze target determination device 10 according to the Variation 6 can accurately determine the gaze object of the user, using that the user's gaze position synchronizes with the movement of the object.

In the Variation 6, multiple objects are arranged and displayed in the horizontal direction, but they do not necessary have to be displayed in such a manner. Furthermore, the display event indicates the movement in a horizontal direction, but it may indicate a movement in a vertical or diagonal direction.

The gaze target determination device according to an aspect of the present invention has been described based on the embodiment and the variations; however, the present invention is not limited to the embodiment and the variations. Those skilled in the art will readily appreciate that many modifications are possible in the exemplary embodiments without materially departing from the novel teachings and advantages of this invention, and therefore, all such modifications are intended to be included within the scope of this invention.

For example, the gaze target determination unit 16 according to the Variation 2 may determine the gaze target while excluding the objects for which the time different less than the latency time is detected.

The gaze target determination device according to an aspect of the present invention has been described based on the embodiment and the variations; however, the present invention may be further modified as below.

(1) Specifically, the gaze target determination device is a computer system including a micro processor, a Read Only Memory (ROM), a Random Access Memory (RAM), a hard-disk unit, a display unit, a keyboard, a mouse, and the like. The RAM or the hard-disk unit stores a computer program. The microprocessor operates according to the computer program, which causes each device to achieve a function thereof. Here, the computer program includes a combination of multiple instruction codes sending an instruction to the computer in order to achieve a predetermined function. It is noted that each device shall not be limited to a computer system including all of a micro processor, a ROM, a RAM, a hard-disk unit, a display unit, a keyboard, and a mouse, but may be a computer system including some of them.

(2) Some or all of the structural elements included in the gaze target determination device may be included in a single system Large Scale Integration (LSI). For example, as shown in FIG. 1, the system LSI 20 includes the gaze direction detection unit 11, the gaze trajectory calculation unit 12, the event setting unit 13, the eye movement event detection unit 14, the synchronization structure analysis unit 15, and the gaze target determination unit 16.

A system LSI is an ultra-multifunction LSI manufactured with plural structural units integrated on a single chip. Specifically, the system LSI is a computer system having a micro processor, a ROM, a RAM, and the like. The RAM stores a computer program. The microprocessor operates according to the computer program, which causes the system LSI to achieve a function thereof.

The system LSI introduced here may be referred to as an Integrated circuit (IC), an LSI, a super LSI, an ultra LSI, depending on integration density. Moreover, a technique of integrating into a circuit shall not be limited to the form of an LSI; instead, integration may be achieved in the form of a designated circuit or a general purpose processor. Employed as well may be the following: a Field Programmable Gate Array (FPGA) which is programmable after manufacturing of the LSI; or a reconfigurable processor which makes possible reconfiguring connections and configurations of circuit cells within the LSI.

In the case where a technique of making an integrated circuit replaces the LSI thanks to advancement in a semiconductor technology or another technique which derives therefrom, such a technique may be employed to integrate functional blocks as a matter of course. Applied as the technique can be biotechnologies.

(3) Some or all of the structural elements included in the gaze target determination device may be included in an IC card or a single module detachable to and from the gaze target determination device. The IC card or the module is a computer system which consists of a micro processor, a ROM, a RAM, and the like. The IC card and the module may also include the ultra-multifunction LSI. The micro processor operates according to the computer program, which allows the IC card and the module to achieve the functions thereof. The IC card and the module may also be tamper-resistant.

(4) The present invention may be a gaze target determination method achieving operations of characteristic structural elements included in the gaze target determination device in steps. The gaze target determination method may be achieved in a form of a computer program executed on a computer or a digital signal including the computer program.

The present invention may further include a computer-readable recording medium which stores the computer program or the digital signal into the followings, for example: a flexible disk; a hard disk; a CD-ROM; a Magneto-Optical disk (MO); a Digital Versatile Disc (DVD); a DVD-ROM; a DVD-RAM; a Blu-ray Disc (BD); and a semi-conductor memory. The present invention may also be the computer program or the digital signal recorded in the recording media.

The present invention may further transmit the computer program or the digital signal via a network and data broadcast mainly including an electronic communications line, a wireless or a wired communications line and the Internet.

The present invention may also be a computer system including a micro processor and a memory. The memory may store the computer program described above, and the micro processor may operate according to the computer program.

The present invention can be implemented by another independent computer system by storing and transferring the program or the digital signal in a recording medium or via a network.

(5) The present invention may be a combination of the above embodiment with any of the above variations.

The gaze target determination device according to an aspect of the present invention is useful, for example, as a device for determining the object at which a user is gazing from among a plurality of objects displayed on a screen.

REFERENCE SIGNS LIST

10 Gaze target determination device
11 Gaze direction detection unit
12 Gaze trajectory calculation unit
13 Event setting unit
14 Eye movement event detection unit
15 Synchronization structure analysis unit
16 Gaze target determination unit
20 System LSI

The invention claimed is:

1. A gaze target determination device, comprising:
a display unit configured to display simultaneously a plurality of objects on a screen, the displayed objects including one target object at which a user is gazing;
an event setting unit configured to generate a display event for each of the displayed objects at different times, the display event triggering a movement of a gaze direction of the user gazing at the displayed object, and indicating at least one of a movement and a change of at least part of the displayed object;
a gaze direction detection unit configured to detect the gaze direction of the user;
a gaze trajectory calculation unit configured to calculate a gaze trajectory that is time series data of the gaze direction, based on the gaze direction detected by the gaze direction detection unit;
an eye movement event detection unit configured to detect an event detection time that is a time at which the gaze direction moves according to the display event, based on the gaze trajectory calculated by the gaze trajectory calculation unit;
a synchronization structure analysis unit configured to calculate, for each of the displayed objects, a time difference between the event detection time detected by the eye movement event detection unit and an event occurrence time that is a time at which the display event is generated by the event setting unit; and
a gaze target determination unit configured to determine the target object at which the user is gazing from among the displayed objects displayed simultaneously on the screen by the display unit, based on the time difference calculated by the synchronization structure analysis unit.

2. The gaze target determination device according to claim 1,
wherein the gaze target determination unit is configured to determine, as the displayed object at which the user is gazing, an object for which a time difference is calculated, the time difference being equal to or greater than a reference time difference and closest to the reference time difference.

3. The gaze target determination device according to claim 1,
wherein the display event triggers a movement of the gaze direction greater than an error in the gaze direction detection performed by the gaze direction detection unit.

4. The gaze target determination device according to claim 1,
wherein the display event indicates a movement of at least part of the displayed object, and
the eye movement event detection unit is configured to detect the event detection time, based on a similarity between a trajectory of the movement indicated by the display event and the gaze trajectory.

5. The gaze target determination device according to claim 4,
wherein the display event indicates a movement including a change of a moving direction, and
the event setting unit is configured to generate the display event by reciprocating at least part of each of the displayed objects.

6. The gaze target determination device according to claim 1,
wherein the display event indicates a movement of at least part of the displayed object in a horizontal direction.

7. The gaze target determination device according to claim 1,
wherein the display event triggers the movement, at a speed equal to or greater than a predetermined speed, of the gaze direction of the user who is gazing at the displayed object, and
the eye movement event detection unit is configured to detect the event detection time which is a time at which the gaze direction moves at a speed equal to or greater than the predetermined speed, based on the gaze trajectory calculated by the gaze trajectory calculation unit.

8. The gaze target determination device according to claim 7,
wherein each of the displayed objects includes a character string,
the display event triggers the movement, at a speed equal to or greater than the predetermined speed, of the gaze direction of the user who is gazing at the displayed object to read the character string, and the event setting unit is configured to generate the display event by changing a character included in the character string from an unreadable state where the user cannot read the character to a readable state where the user can read the character.

9. The gaze target determination device according to claim 8, wherein the display event indicates a change of an initial character included in the character string, from the unreadable state to the readable state, and the event setting unit is configured to generate the display event by changing the character included in the character string from the readable state to the unreadable state, and changing the initial character included in the character string from the unreadable state to the readable state.

10. An integrated circuit for gaze target determination, comprising:

a display unit configured to display simultaneously a plurality of objects on a screen, the displayed objects including one target object at which a user is gazing;

an event setting unit configured to generate a display event for each of the display objects at different times, the display event triggering a movement of a gaze direction of the user gazing at the displayed object, and indicating at least one of a movement and a change of at least part of the displayed object;

a gaze direction detection unit configured to detect the gaze direction of the user;

a gaze trajectory calculation unit configured to calculate a gaze trajectory that is time series data of the gaze direction, based on the gaze direction detected by the gaze direction detection unit;

an eye movement event detection unit configured to detect an event detection time that is a time at which the gaze direction moves according to the display event, based on the gaze trajectory calculated by the gaze trajectory calculation unit;

a synchronization structure analysis unit configured to calculate, for each of the displayed objects, a time difference between the event detection time detected by the eye movement event detection unit and an event occurrence time that is a time at which the display event is generated by the event setting unit; and a gaze target determination unit configured to determine the target object at which the user is gazing from among the displayed objects displayed simultaneously on the screen by the display unit, based on the time difference calculated by the synchronization structure analysis unit.

11. A method of gaze target determination, comprising:

displaying simultaneously, using a display unit, a plurality of objects on a screen, the displayed objects including one target object at which a user is gazing;

generating a display event for each of the displayed objects at different times, the display event triggering a movement of a gaze direction of the user gazing at the displayed object, and indicating at least one of a movement and a change of at least part of the displayed object;

detecting the gaze direction of the user;

calculating a gaze trajectory that is time series data of the gaze direction, based on the gaze direction detected;

detecting an event detection time that is a time at which the gaze direction moves according to the display event, based on the gaze trajectory calculated;

calculating, for each of the displayed objects, a time difference between the event detection time detected and an event occurrence time that is a time at which the display event is generated; and determining the target object at which the user is gazing from among the displayed objects displayed simultaneously on the screen, based on the time difference calculated.

12. A non-transitory computer-readable recording medium storing a program for causing a computer to execute the method of gaze target determination according to claim 11.

* * * * *